(12) United States Patent
Ozaki et al.

(10) Patent No.: US 8,770,945 B2
(45) Date of Patent: Jul. 8, 2014

(54) CENTRIFUGAL PUMP APPARATUS

(75) Inventors: Takayoshi Ozaki, Iwata (JP); Hiroyuki Yamada, Iwata (JP); Kenichi Suzuki, Iwata (JP); Ken Sugiura, Iwata (JP)

(73) Assignee: Thoratec Corporation, Pleasanton, CA (US)

( * ) Notice: Subject to any disclaimer, the term of this patent is extended or adjusted under 35 U.S.C. 154(b) by 379 days.

(21) Appl. No.: 13/254,979

(22) PCT Filed: Mar. 1, 2010

(86) PCT No.: PCT/JP2010/053221
§ 371 (c)(1),
(2), (4) Date: Sep. 6, 2011

(87) PCT Pub. No.: WO2010/101107
PCT Pub. Date: Sep. 10, 2010

(65) Prior Publication Data
US 2011/0318203 A1  Dec. 29, 2011

(30) Foreign Application Priority Data

Mar. 6, 2009 (JP) ................. 2009-053661
May 8, 2009 (JP) ................. 2009-113753

(51) Int. Cl.
*A61M 1/10* (2006.01)
(52) U.S. Cl.
USPC ............. 417/44.1; 604/151; 604/264
(58) Field of Classification Search
CPC .......... A61M 1/101; A61M 2001/1015; A61M 2001/1017
USPC ........ 417/44.11, 417, 420; 415/900; 604/151, 604/264
See application file for complete search history.

(56) References Cited

U.S. PATENT DOCUMENTS

| | | | |
|---|---|---|---|
| 5,947,703 A | 9/1999 | Nojiri et al. | |
| 6,074,180 A | 6/2000 | Khanwilkar et al. | |
| 6,264,635 B1 | 7/2001 | Wampler et al. | |
| 6,698,097 B1 | 3/2004 | Miura et al. | |
| 2005/0287022 A1 | 12/2005 | Yaehashi et al. | |
| 2006/0024182 A1 | 2/2006 | Akdis et al. | |
| 2008/0030895 A1 | 2/2008 | Obara et al. | |
| 2008/0124231 A1 | 5/2008 | Yaegashi | |
| 2009/0074336 A1 | 3/2009 | Engesser et al. | |

FOREIGN PATENT DOCUMENTS

| | | |
|---|---|---|
| EP | 1113117 A2 | 7/2001 |
| JP | 04-091396 | 3/1992 |
| JP | 6-53790 | 7/1994 |

(Continued)

OTHER PUBLICATIONS

European Search Report issued in European Patent Application No. 10748702.7 dated Apr. 2, 2013.

*Primary Examiner* — Charles Freay
*Assistant Examiner* — Patrick Hamo
(74) *Attorney, Agent, or Firm* — Kilpatrick Townsend & Stockton LLP

(57) ABSTRACT

In this centrifugal blood pump apparatus, one permanent magnet is provided in one surface of an impeller, a second permanent magnet is provided in an inner wall of a blood chamber, a third permanent magnet is provided in the other surface of the impeller, and a fourth permanent magnet and a rotor for driving the impeller to rotate are provided, with an diaphragm being interposed. An amount of change in attractive force between the first permanent magnet and the second permanent magnet and an amount of change in attractive force between the third and fourth permanent magnets when the impeller is eccentric are made substantially equal to each other. Therefore, a levitation position of the impeller can always be maintained at a substantially central position in a housing.

21 Claims, 25 Drawing Sheets

(56) References Cited

FOREIGN PATENT DOCUMENTS

| JP | 2004-209240 | 7/2004 |
|----|-------------|--------|
| JP | 2006-167173 | 6/2006 |
| JP | 2007-089972 | 4/2007 |
| JP | 2007-089974 | 4/2007 |
| WO | 97/42413 A1 | 11/1997 |
| WO | 2005/034312 A2 | 4/2005 |

CENTRIFUGAL PUMP APPARATUS

RELATED APPLICATIONS

This application is the U.S. National Phase under 35 U.S.C. §371 of International Application No. PCT/JP2010/053221, filed on Mar. 1, 2010, which in turn claims the benefit of Japanese Application Nos. 2009-053661, filed on Mar. 6, 2009 and 2009-113753, filed on May 8, 2009, the disclosures of which Applications are incorporated by reference herein.

TECHNICAL FIELD

The present invention relates to a centrifugal pump apparatus, and particularly to a centrifugal pump apparatus including an impeller for delivering liquid by centrifugal force during rotation.

BACKGROUND ART

In recent years, a centrifugal blood pump apparatus in which driving torque from an external motor is transmitted to an impeller in a blood chamber through magnetic coupling has increasingly been used as a blood circulation apparatus of an artificial heart-lung machine. According to such a centrifugal blood pump apparatus, physical contact between the blood chamber and the outside can be eliminated, thus preventing invasion of bacteria and the like into blood.

A centrifugal blood pump in PTL 1 (Japanese Patent Laying-Open No. 2004-209240) includes a housing having first to third chambers partitioned from one another by first and second diaphragms, an impeller rotatably provided in the second chamber (blood chamber), a magnetic element provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic hearing is formed in a surface of the second diaphragm facing the other surface of the impeller. Owing to attractive force acting on the one surface of the impeller from the electromagnet, attractive force acting on the other surface of the impeller from the permanent magnet in the rotor, and a hydrodynamic bearing effect of the grooves for hydrodynamic bearing, the impeller moves away from an inner surface of the second chamber and rotates without contacting.

A centrifugal blood pump in PTL 2 (Japanese Patent Laying-Open No. 2006-167173) includes a housing having first to third chambers partitioned from one another by first and second diaphragms, an impeller rotatably provided in the second chamber (blood chamber), a magnetic element provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first hydrodynamic bearing is formed in a surface of the first diaphragm facing the one surface of the impeller, and a second groove for hydrodynamic bearing is formed in a surface of the second diaphragm facing the other surface of the impeller. Owing to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner surface of the second chamber and rotates without contacting.

A turbo-type pump in FIGS. 8 and 9 of PTL 3 (Japanese Patent Laying-Open No. 4-91396) includes a housing, an impeller rotatably provided in the housing, a first permanent magnet provided in one surface of the impeller, a rotor provided outside the housing, a second permanent magnet provided in the rotor to face the one surface of the impeller, a third permanent magnet provided in the other surface of the impeller, and a magnetic element provided in the housing to face the other surface of the impeller. A first groove for hydrodynamic bearing is formed in the one surface of the impeller, and a second groove for hydrodynamic bearing is formed in the other surface of the impeller. Owing to attractive force acting on the one surface of the impeller from the second permanent magnet in the rotor, attractive force acting on the other surface of the impeller from the magnetic element in the housing, and a hydrodynamic bearing effect of the first and second grooves for hydrodynamic bearing, the impeller moves away from an inner surface of the housing and rotates without contacting.

A clean pump in PTL 4 (Japanese Utility Model Laying-Open No. 6-53790) includes a casing, an impeller rotatably provided in the casing, a first permanent magnet provided in one surface of the impeller, a rotor provided outside the casing, a second permanent magnet provided in the rotor to face the one surface of the impeller, a magnetic element provided in the other surface of the impeller, and an electromagnet provided outside a housing to face the other surface of the impeller. A groove for hydrodynamic bearing is formed in the one surface of the impeller.

The electromagnet is actuated when a rotation speed of the impeller is lower than a prescribed rotation speed, and power supply to the electromagnet is stopped when the rotation speed of the impeller becomes higher than the prescribed rotation speed. Owing to attractive force acting on the one surface of the impeller from the second permanent magnet in the rotor and a hydrodynamic bearing effect of the groove for hydrodynamic bearing, the impeller moves away from an inner surface of the housing and rotates without contacting.

CITATION LIST

Patent Literature

PTL 1: Japanese Patent Laying-Open No. 2004-209240
PTL 2: Japanese Patent Laying-Open No. 2006-167173
PTL 3: Japanese Patent Laying-Open No. 4-91396
PTL 4: Japanese Utility Model Laying-Open No. 6-53790

SUMMARY OF INVENTION

Technical Problem

The pumps in PTLs 1 to 4 described above are common in the feature of axially (in a direction of a rotation axis of the impeller) supporting the impeller by the grooves for hydrodynamic hearing formed in a portion where the impeller and the housing face each other and radially (in a direction of a radius of the impeller) supporting the impeller by the attractive force between the permanent magnet provided in the impeller and the permanent magnet provided outside the housing.

In such a centrifugal pump apparatus, when rigidity for supporting the impeller (force required for moving the impeller by a unit length) is low, the impeller comes in contact with the inner wall of the blood chamber by application of vibration (accelerated vibration) involved with a user's operation. Therefore, supporting rigidity sufficiently high in each of the axial direction and the radial direction is required.

In order to increase rigidity for supporting the impeller, magnetic coupling force between the permanent magnet in the impeller and the permanent magnet on the housing side should only be increased. It is not easy, however, to increase that magnetic coupling force. Namely, in a hydrodynamic bearing type centrifugal pump apparatus, initially, a flow rate, a pump head (pressure), and a minimum value of an interval between the blood chamber and the impeller are provided as the specifications. Then, a diameter of the impeller determines a rotation speed and a dimension of a groove for hydrodynamic bearing.

When the dimension of the groove for hydrodynamic bearing, the diameter of the impeller, the rotation speed, and the interval between the blood chamber and the impeller are determined, a load capacity is determined and hence magnetic coupling force balanced therewith is determined. When magnetic coupling force is determined, rigidity for supporting the impeller is also determined. Therefore, though it is necessary to increase the load capacity in order to increase rigidity for supporting the impeller, increase in the load capacity is limited, because the load capacity is dependent on viscosity of blood, a rotation speed of the impeller, a dimension of a groove for hydrodynamic bearing, and an interval between the blood chamber and the impeller.

In addition, a gap between an end surface of the impeller and an inner surface of the housing on which hydrodynamic pressure acts is formed on a side of an impeller rotational torque generation portion and on a side of an impeller auxiliary attracting portion. These gaps being substantially equal to each other means a greatest distance between the end surface of the impeller and the inner surface of the housing. Thus, even when disturbance force acts on the impeller, it is less likely that the end surface of the impeller comes in contact with the inner surface of the housing. In a single volute pump construction or a pump construction where there is no volute and a blood outlet port is arranged in contact with a cylindrical housing, however, unbalance in pressure in a pump chamber is caused during a desired pump operation and the impeller moves in a radial direction in such a manner that it is attracted toward the blood outlet port. Then, attractive force in the axial direction at both end surfaces of the impeller becomes smaller.

Therefore, when an amount of change in attractive force in the axial direction with respect to displacement in the radial direction of the impeller rotational torque generation portion is different from an amount of change in attractive force in the axial direction with respect to displacement in the radial direction of a magnetic coupling portion formed in the impeller auxiliary attracting portion, a position where attractive forces in the axial direction are balanced with each other is displaced from the substantially central position in the housing during the desired pump operation. Consequently, one of the gaps between the end surface of the impeller and the inner surface of the housing on both sides becomes narrower and the other of them becomes wider. On the side where the gap has become narrower, even small disturbance force acting on the impeller readily causes contact between the end surface of the impeller and the inner surface of the housing.

In view of the above, a main object of the present invention is to provide a centrifugal pump apparatus having resistance to disturbance acting on an impeller, in which a gap for levitation between the impeller and a housing is not varied even when the impeller radially moves in the housing.

Solution to Problem

A centrifugal pump apparatus according to the present invention is a centrifugal pump apparatus including a housing having first and second chambers partitioned from each other by a diaphragm, an impeller rotatably provided in the first chamber along the diaphragm, for delivering liquid by centrifugal force during rotation, and drive means provided in the second chamber for driving the impeller to rotate with the diaphragm being interposed, and it includes a first magnetic element provided in one surface of the impeller, a second magnetic element provided in an inner wall of the first chamber facing the one surface of the impeller, for attracting the first magnetic element, and a third magnetic element provided in the other surface of the impeller. During rotation of the impeller, first attractive force between the first and second magnetic elements and second attractive force between the third magnetic element and the drive means are balanced with each other substantially in a center of a movable range of the impeller in the first chamber. An amount of change in the first attractive force with respect to an amount of eccentricity in a radial direction of the impeller is substantially equal to an amount of change in the second attractive force with respect to the amount of eccentricity in the radial direction of the impeller. A first groove for hydrodynamic bearing is formed in the one surface of the impeller or in the inner wall of the first chamber facing the one surface, and a second groove for hydrodynamic bearing is formed in the other surface of the impeller or in the diaphragm facing the other surface.

Preferably, the drive means includes a rotor rotatably provided along the diaphragm in the second chamber, a fourth magnetic element provided in the rotor, for attracting the third magnetic element, and a motor for rotating the rotor.

Further preferably, an absolute value of a positive supporting rigidity value in the radial direction of a magnetic coupling portion constituted of the first and second magnetic elements is greater than an absolute value of a positive supporting rigidity value in a radial direction of a magnetic coupling portion constituted of the third and fourth magnetic elements.

Further preferably, the third magnetic element includes a plurality of magnets arranged along the same circle such that adjacent magnetic polarities are different from each other, and the drive means includes a plurality of coils provided to face the plurality of magnets, for generating rotating magnetic field.

Further preferably, the third magnetic element includes a plurality of magnets arranged along the same circle such that adjacent magnetic polarities are different from each other. The drive means includes a plurality of fourth magnetic elements provided to face the plurality of magnets and a plurality of coils provided in correspondence with the plurality of fourth magnetic elements respectively and each wound around the corresponding fourth magnetic element, for generating rotating magnetic field.

Further preferably, the second attractive force is adjusted by varying a phase of a current fed to the plurality of coils.

Further preferably, the centrifugal pump apparatus further includes a magnetic sensor provided in the second chamber to face the plurality of magnets, and a phase of a current fed to the plurality of coils is varied based on an output signal from the magnetic sensor.

Further preferably, the centrifugal pump apparatus further includes a plurality of the first magnetic elements provided in one surface of the impeller and aligned in a radial direction of the impeller and a plurality of the second magnetic elements provided in the inner wall of the first chamber facing the one surface of the impeller and attracting the plurality of first magnetic elements respectively. During rotation of the impeller, first attractive force between the plurality of first magnetic elements and the plurality of second magnetic elements and second attractive force between the third magnetic element and the drive unit are balanced with each other substantially in the center of the movable range of the impeller in the first chamber.

Further preferably, at least one magnetic element of the plurality of first magnetic elements and the plurality of second magnetic elements is formed annularly around a rotation centerline of the impeller.

Further preferably, at least one magnetic element of the plurality of first magnetic elements and the plurality of second magnetic elements are formed as multiple pieces annularly around a rotation centerline of the impeller.

Further preferably, each of the plurality of first magnetic elements and the plurality of second magnetic elements is a permanent magnet, and N poles of two first magnetic elements adjacent in the radial direction of the impeller are oriented in an identical direction.

Further preferably, each of the plurality of first magnetic elements and the plurality of second magnetic elements is a permanent magnet, and N poles of two first magnetic elements adjacent in the radial direction of the impeller are oriented in directions different from each other.

Further preferably, an interval between two first magnetic elements adjacent in the radial direction of the impeller is greater than ½ of a movable distance of the impeller in the radial direction in the first chamber. In this case, even when the impeller moves in the radial direction to a maximum extent, magnetic interference between two adjacent pairs of first and second magnetic elements can be avoided.

Further preferably, a plurality of the third magnetic elements are provided, and the plurality of third magnetic elements are arranged along the same circle such that adjacent magnetic polarities are different from each other. The drive means includes a plurality of coils provided in correspondence with the plurality of third magnetic elements respectively, for generating rotating magnetic field.

Further preferably, a plurality of the third magnetic elements are provided, and the plurality of third magnetic elements are arranged along the same circle such that adjacent magnetic polarities are different from each other. The drive means includes a plurality of fourth magnetic elements arranged to face the plurality of third magnetic elements and a plurality of coils provided in correspondence with the plurality of fourth magnetic elements respectively and each wound around the corresponding fourth magnetic element, for generating rotating magnetic field.

Further preferably, the drive means includes a rotor rotatably provided along the diaphragm in the second chamber, a fourth magnetic element provided in the rotor to face the third magnetic element for attracting the third magnetic element, and a motor for rotating the rotor.

Further preferably, the liquid is blood and the centrifugal pump apparatus is used for circulating the blood. In this case, the impeller is smoothly activated to rotate and a distance between the impeller and the housing is secured, thereby preventing occurrence of hemolysis.

Advantageous Effects of Invention

In the centrifugal pump apparatus according to the present invention, first and second attractive forces acting on the impeller are balanced with each other substantially in the center of the movable range of the impeller, amounts of change in the first and second attractive forces with respect to an amount of eccentricity in the radial direction of the impeller are made substantially equal to each other, and first and second grooves for hydrodynamic bearing are formed. Therefore, even when the impeller moves in the radial direction in the housing, a gap for levitation between the impeller and the housing is not varied and thus resistance to disturbance acting on the impeller can be improved.

DESCRIPTION OF EMBODIMENTS

[First Embodiment]

Figure 1:
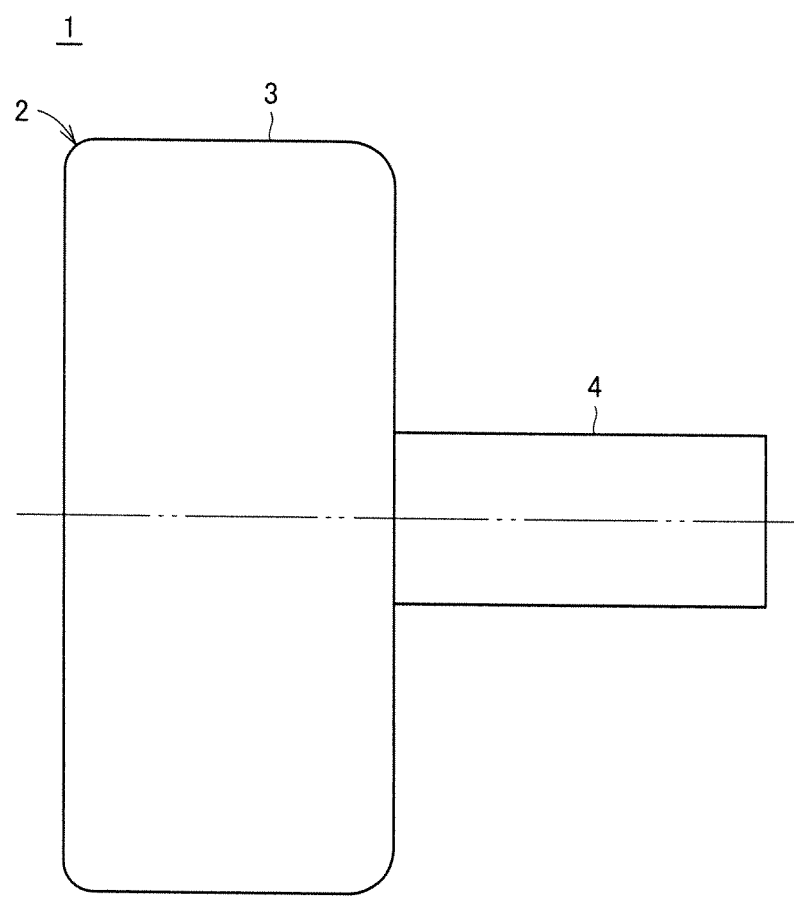
FIG. 1 is a front view showing the appearance of a pump unit of a centrifugal blood pump apparatus according to a first embodiment of the present invention.
Figure 2:
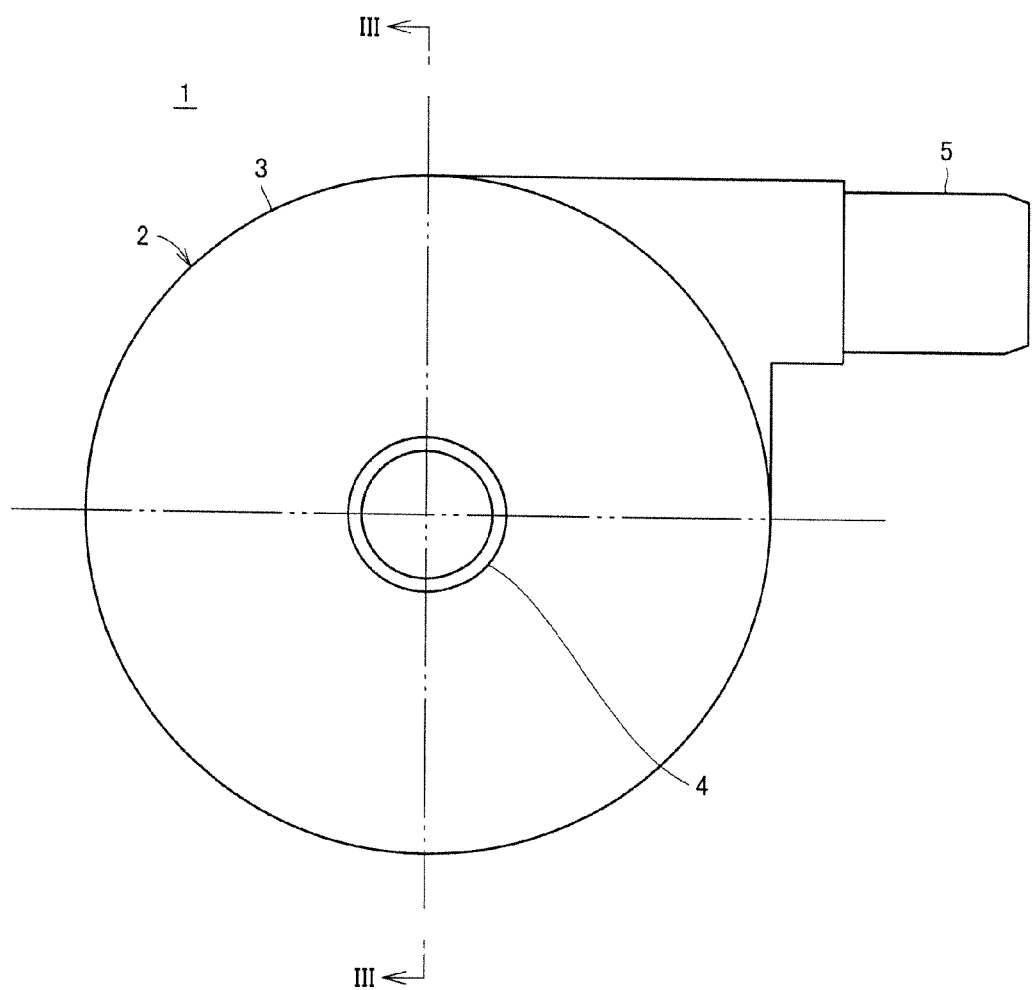
FIG. 2 is a side view of the pump unit shown in FIG. 1.

As shown in FIGS. 1 and 2, a pump unit 1 of a centrifugal blood pump apparatus according to a first embodiment includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
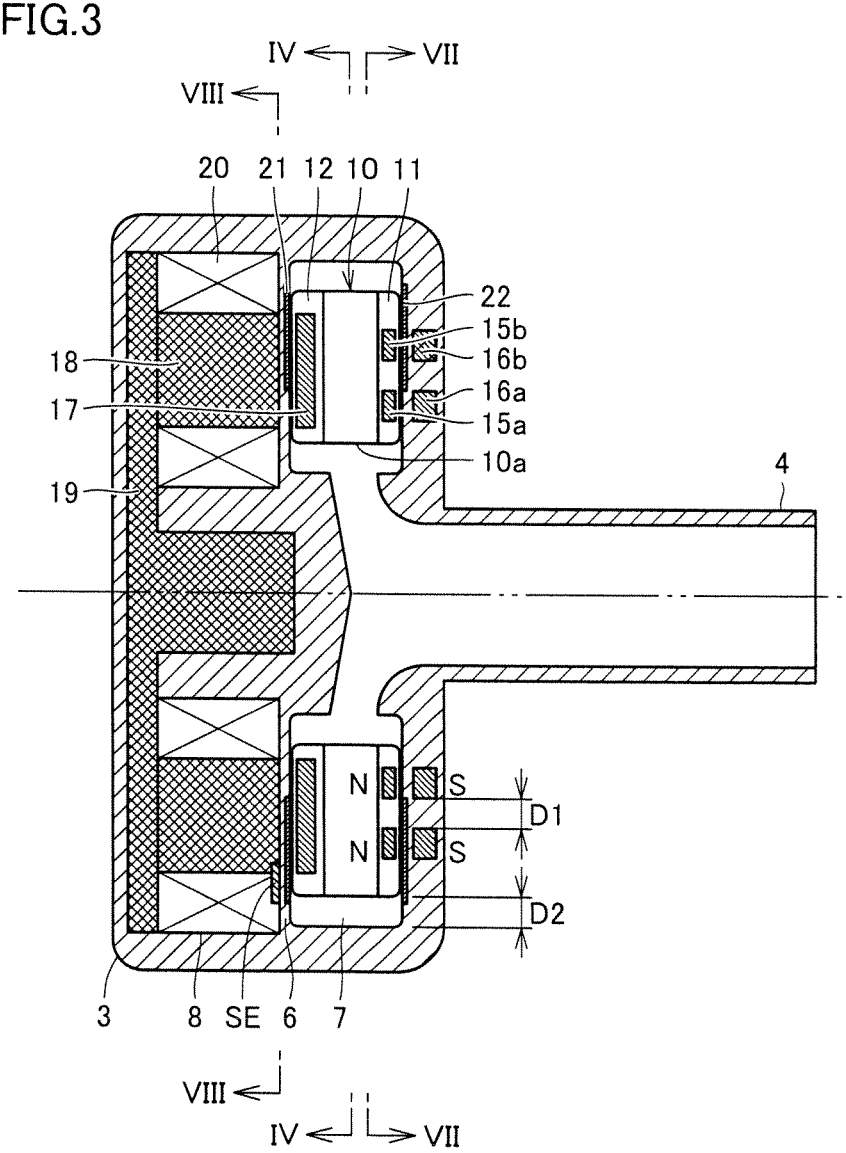
FIG. 3 is a cross-sectional view along the line in FIG. 2.
Figure 4:
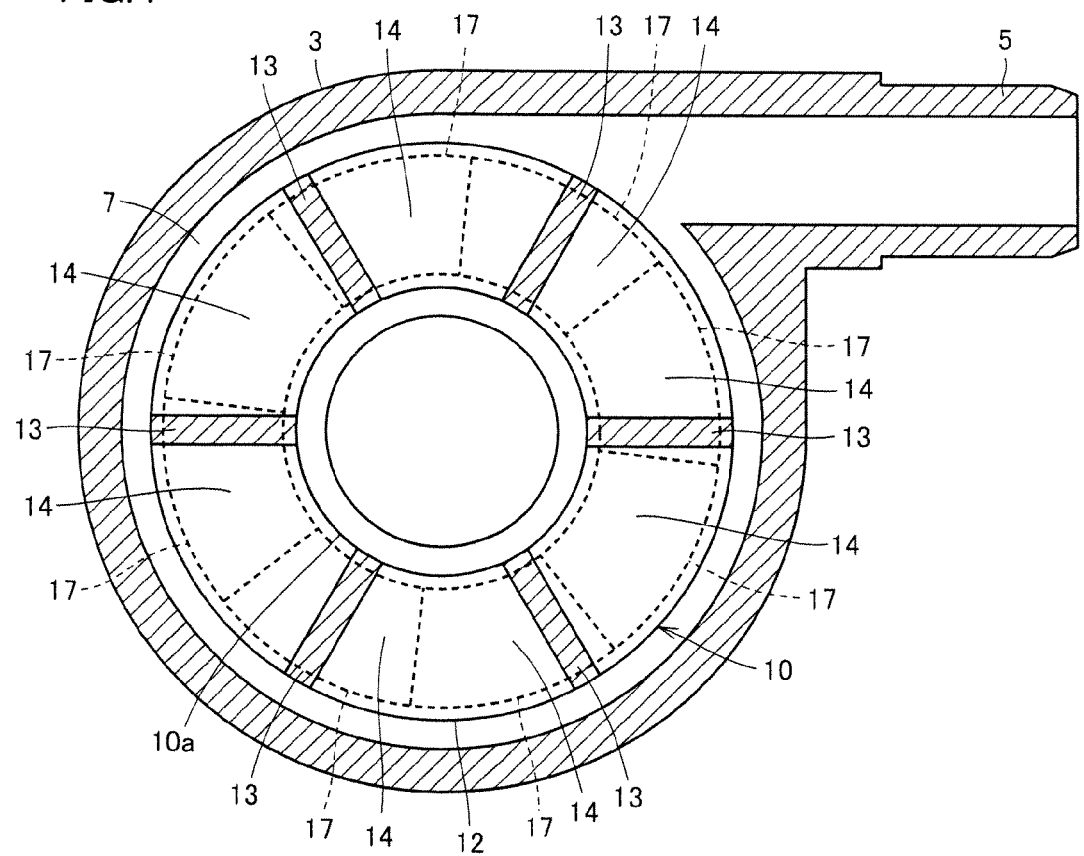
FIG. 4 is a cross-sectional view along the line IV-IV in FIG. 3.

In housing 2, as shown in FIG. 3, a blood chamber 7 and a motor chamber 8 partitioned from each other by a diaphragm 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side and shroud 12 is arranged on the diaphragm 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a in the center of impeller 10, and it extends with through hole 10a in impeller 10 as a starting point to an outer circumference such that blood passage 14 gradually increases in width. In other words, vane 13 is formed between two adjacent blood passages 14. In the first embodiment, the plurality of vanes 13 are formed at regular angular intervals, and they have the same shape. Thus, the plurality of blood passages 14 are provided at regular angular intervals and they have the same shape.

When impeller 10 is driven to rotate, blood that has flowed in through blood inlet port 4 is delivered by centrifugal force from through hole 10a to an outer circumferential portion of impeller 10 via blood passages 14 and it flows out through blood outlet port 5.

Permanent magnets 15a, 15b are embedded in shroud 11 and permanent magnets 16a, 16b for attracting permanent magnets 15a, 15b respectively are embedded in an inner wall of blood chamber 7 facing shroud 11. Permanent magnets 15a, 15b, 16a, and 16b are provided to attract (in other words, bias) impeller 10 to the side opposite to motor chamber 8, that is, toward blood inlet port 4.

Figure 5:
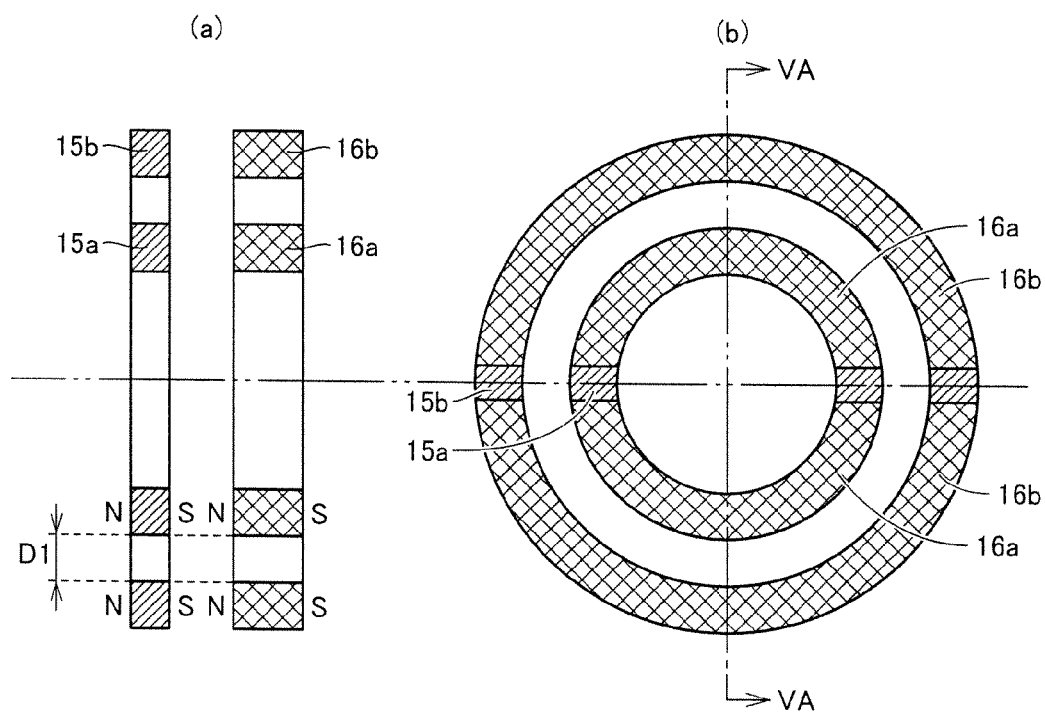
FIG. 5 is a diagram showing a permanent magnet shown in FIG. 3.

FIGS. 5 (a) and (b) are diagrams showing a structure of permanent magnets 15a, 15b, 16a, and 16b and FIG. 5 (a) is a cross-sectional view along the line VA-VA in FIG. 5 (b). As shown in FIGS. 5 (a) and (b), each of permanent magnets 15a, 15b is formed annularly, and an outer diameter of permanent magnet 15a is smaller than an inner diameter of permanent magnet 15b. Permanent magnets 15a, 15b are coaxially provided, and central points of respective permanent magnets 15a, 15b are both arranged on a rotation centerline of impeller 10. Though end surfaces of respective permanent magnets 15a, 15b in the same direction have the same polarity in the figure, they may be constructed to be different in polarity.

On the other hand, each of permanent magnets 16a, 16b is formed in an arc shape, and two permanent magnets are aligned in a direction of rotation of impeller 10. An outer diameter and an inner diameter of two permanent magnets 16a arranged annularly are the same as the outer diameter and the inner diameter of permanent magnet 15a, respectively. An outer diameter and an inner diameter of two permanent magnets 16b arranged annularly are the same as the outer diameter and the inner diameter of permanent magnet 15b, respectively. Though end surfaces of respective permanent magnets 16a, 16b in the same direction have the same polarity in the figure, they may be constructed to be different in polarity. Permanent magnets 15a and 16a face each other and permanent magnets 15b and 16b face each other, in such polarity arrangement as one attracting the other.

In addition, as shown in FIG. 3, an interval between permanent magnets 15a and 15b (that is, an interval between permanent magnets 16a and 16b) D1 is set to be greater than a distance D2 which is half a movable distance of impeller 10 in the radial direction (that is, a distance of a difference between the inner diameter of blood chamber 7 and the outer diameter of impeller 10) (D1>D2). This is because, when impeller 10 moves in the radial direction to a maximum extent while relation of D1<D2 is satisfied, permanent magnets 15a and 16b interfere with each other and permanent magnets 15b and 16a interfere with each other and hence returning force for returning impeller 10 to a central position of the pump becomes unstable.

Since two pairs of permanent magnets 15a and 16a and permanent magnets 15b and 16b are thus provided in the radial direction of impeller 10, rigidity for supporting impeller 10 in the radial direction can be increased as compared with a case where only a pair of permanent magnets is provided in the radial direction of impeller 10.

Instead of providing permanent magnets 15a, 15b and permanent magnets 16a, 16b in shroud 11 and the inner wall of blood chamber 7, respectively, a permanent magnet may be provided in one of shroud 11 and the inner wall of blood chamber 7, and a magnetic element may be provided in the other. Either a soft magnetic element or a hard magnetic element may be used as the magnetic element.

Though FIG. 3 shows a case where opposing surfaces of permanent magnets 15a and 16a are identical in size and opposing surfaces of permanent magnets 15b and 16b are identical in size, in order to prevent lowering in rigidity of impeller 10 due to attractive force of permanent magnets 15a, 15b and permanent magnets 16a, 16b, preferably, opposing surfaces of permanent magnets 15a and 16a are different in size from each other and opposing surfaces of permanent magnets 15b and 16b are different in size from each other. By differing the size of the opposing surfaces of permanent magnets 15a, 15b and permanent magnets 16a, 16b, an amount of change in attractive force, that is, negative rigidity, which varies depending on a distance therebetween, can be suppressed to be small and lowering in rigidity for supporting impeller 10 can be prevented.

In FIGS. 5 (a) and (b), each of permanent magnets 15a, 15b is annularly formed, and each of permanent magnets 16a, 16b is formed in an arc shape and two of the permanent magnets are aligned at regular angular intervals in a direction of rotation of impeller 10. In contrast, however, each of permanent magnets 16a, 16b may be formed annularly, and each of permanent magnets 15a, 15b may be formed in an arc shape and two of the permanent magnets may be aligned at regular angular intervals in a direction of rotation of impeller 10. Alternatively, each of permanent magnets 15a, 15b or each of permanent magnets 16a, 16b may be formed in a shorter arc shape and a plurality of the permanent magnets may be aligned at regular angular intervals in a direction of rotation of impeller 10.

As shown in FIGS. 3 and 4, a plurality of (e.g., eight) permanent magnets 17 are embedded in shroud 12. The plurality of permanent magnets 17 are arranged at regular angular intervals along the same circle such that adjacent magnetic polarities thereof are different from each other. In other words, permanent magnet 17 having the N-pole toward motor chamber 8 and permanent magnet 17 having the S-pole toward motor chamber 8 are alternately arranged at regular angular intervals along the same circle.

Figure 8:
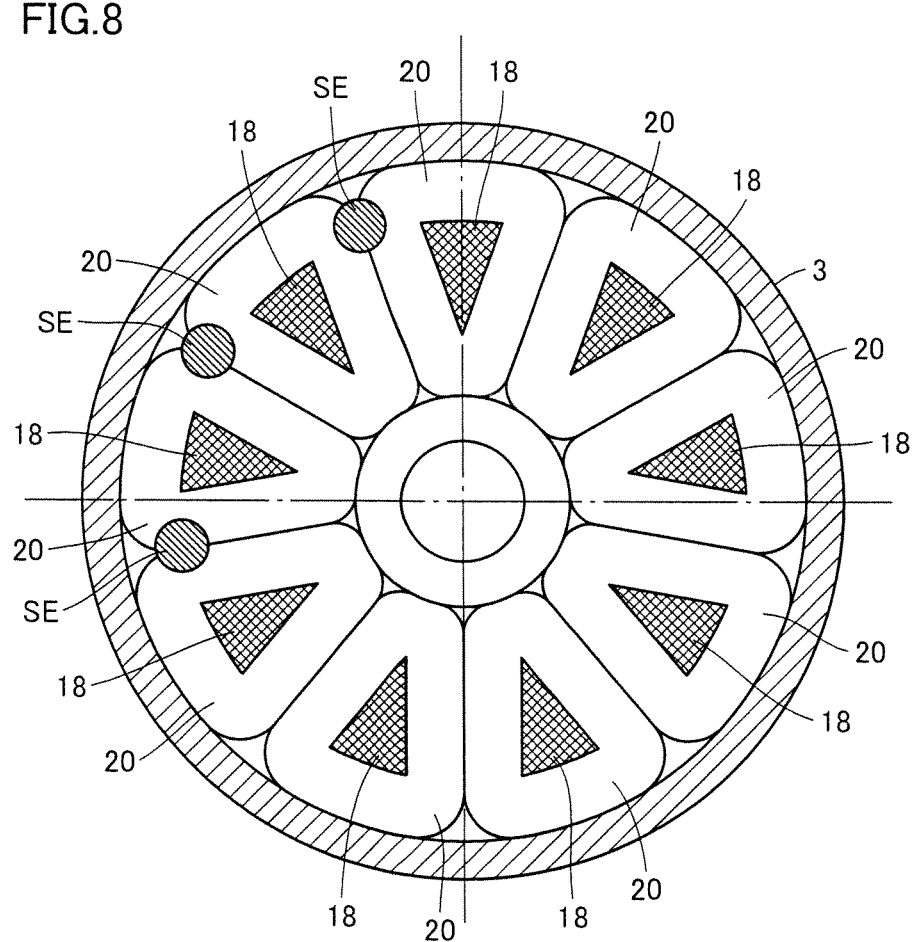
FIG. 8 is a cross-sectional view along the line VIII-VIII in FIG. 3.

As shown in FIGS. 3 and 8, a plurality of (e.g., nine) magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped yoke 19. A coil 20 is wound around each magnetic element 18.

Figure 9:
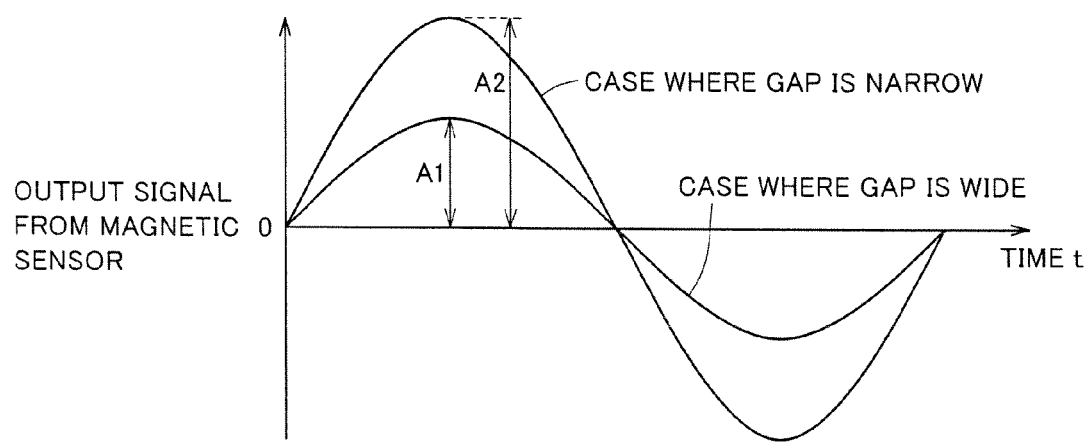
FIG. 9 is a time chart showing an operation of a magnetic sensor shown in FIG. 8.

Three magnetic sensors SE are provided among four adjacent magnetic elements 18 among nine magnetic elements 18. Three magnetic sensors SE are arranged to face paths in impeller 10, through which the plurality of permanent magnets 17 pass. As impeller 10 rotates and the S pole and the N pole of the plurality of permanent magnets 17 alternately pass by the vicinity of magnetic sensor SE, a level of an output signal from magnetic sensor SE varies sinusoidally as shown in FIG. 9. Therefore, by detecting temporal change in the output signal from magnetic sensor SE, positional relation between the plurality of permanent magnets 17 and the plurality of magnetic elements 18 can be detected and timing to feed a current to the plurality of coils 20 and the rotation speed of impeller 10 can be found.

When a gap between impeller 10 and diaphragm 6 is wide, magnetic field in the vicinity of magnetic sensor SE becomes weak and an amplitude A1 of the output signal from magnetic sensor SE becomes small. When the gap between impeller 10 and diaphragm 6 is narrow, magnetic field in the vicinity of magnetic sensor SE becomes strong and an amplitude A2 of the output signal from magnetic sensor SE becomes great. Therefore, by detecting an amplitude of the output signal from magnetic sensor SE, a position of impeller 10 in the movable range of impeller 10 can be detected.

Figure 10:
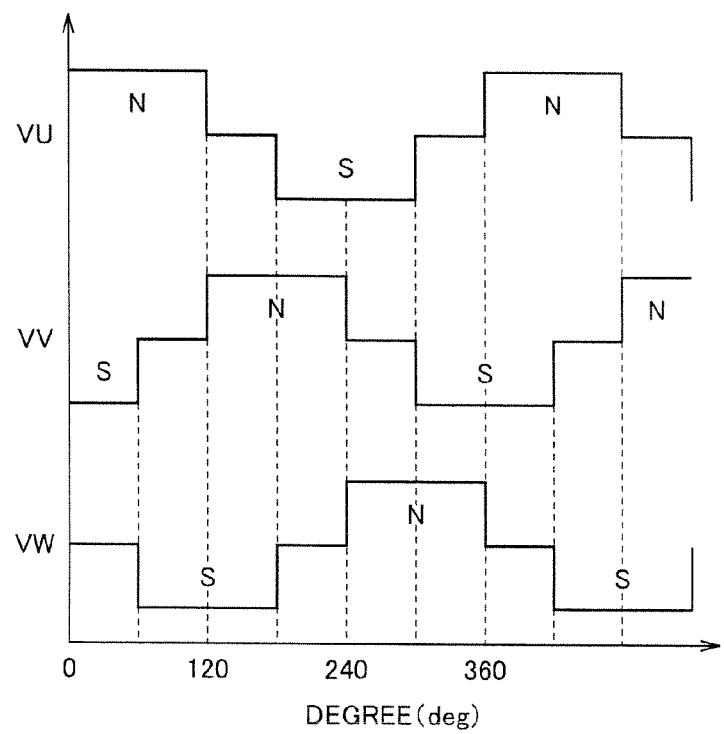
FIG. 10 is a time chart illustrating voltages applied to a plurality of coils shown in FIG. 8.

Voltages are applied to nine coils 20 in a power distribution system shifted by 120 degrees, for example. That is, nine coils 20 are divided into groups each including three coils. Voltages VU, VV and VW as shown in FIG. 10 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees and becomes the S-pole during the period of 180 to 300 degrees. Voltage VV is delayed in phase from voltage VU by 120 degrees, and voltage VW is delayed in phase from voltage VV by 120 degrees. Thus, rotating magnetic field can be formed by applying voltages VU, VV and VW to first to third coils 20, respectively, so that impeller 10 can be rotated by attractive force and repulsion force between the plurality of magnetic elements 18 and the plurality of permanent magnets 17 in impeller 10.

When impeller 10 is rotating at a rated rotation speed, attractive force between permanent magnets 15a, 15b and permanent magnets 16a, 16b and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be lowered. In addition, a surface of impeller 10 and a surface of an inner wall of housing 2 are not damaged (no projections and recesses in the surfaces) during the relative slide, and moreover, impeller 10 is readily levitated from housing 2 without contacting even when hydrodynamic pressure is low during low-speed rotation. Accordingly, occurrence of hemolysis due to the relative slide between impeller 10 and housing 2 or occurrence of thrombus due to small damage (projections and recesses) to the surfaces which occurs during the relative slide is avoided.

A plurality of grooves for hydrodynamic bearing 21 are formed in a surface of diaphragm 6 facing shroud 12 of impeller 10, and a plurality of grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

Figure 6:
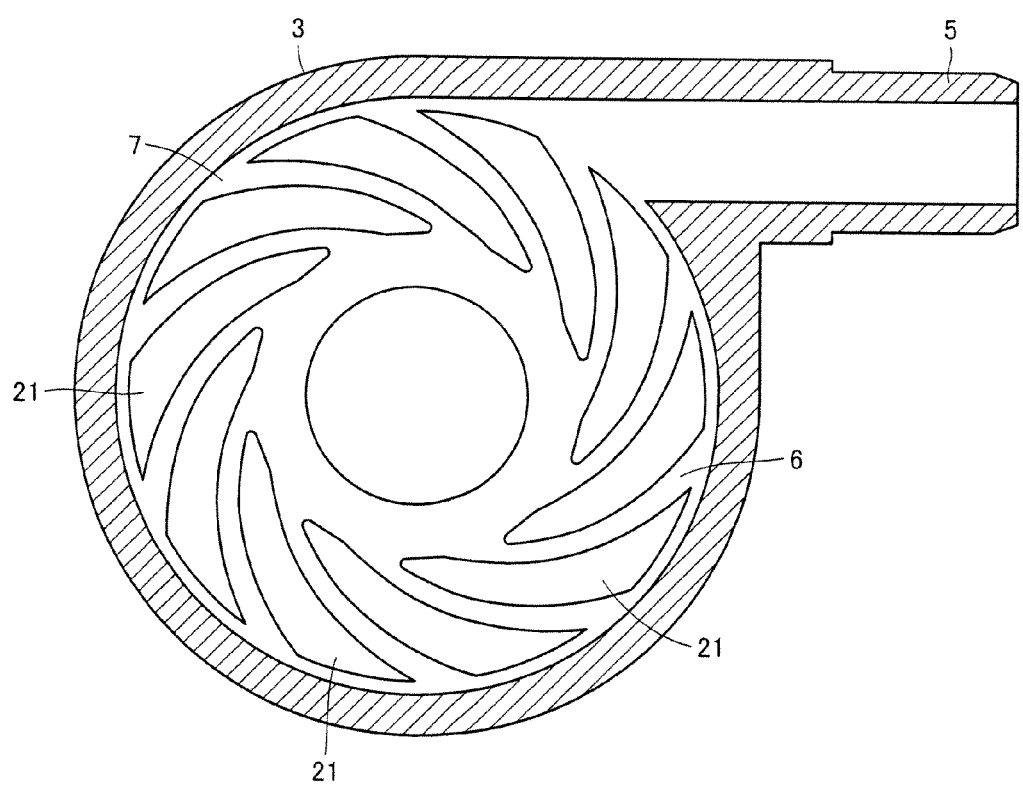
FIG. 6 is a cross-sectional view showing a state where an impeller has been removed from the cross-sectional view along the line IV-IV in FIG. 3.

Specifically, as shown in FIG. 6, the plurality of grooves for hydrodynamic hearing 21 are each formed with a size corresponding to shroud 12 of impeller 10. Each of grooves for hydrodynamic bearing 21 has one end on an edge (circumference) of a circular portion slightly distant from a center of diaphragm 6, and extends spirally (in other words, in a curved manner) toward a portion near an outer edge of diaphragm 6 such that groove for hydrodynamic bearing 21 gradually increases in width. The plurality of grooves for hydrodynamic bearing 21 have substantially the same shape, and they are arranged at substantially regular intervals. Groove for hydrodynamic bearing 21 is a concave portion, and it preferably has a depth of about 0.005 to 0.4 mm. It is preferable that about 6 to 36 grooves for hydrodynamic bearing 21 be provided.

In FIG. 6, ten grooves for hydrodynamic bearing 21 are arranged equiangularly with respect to a central axis of impeller 10. Since groove for hydrodynamic bearing 21 has a so-called inward spiral groove shape, clockwise rotation of impeller 10 causes increase in liquid pressure from an outer diameter portion toward an inner diameter portion of groove for hydrodynamic hearing 21. As a result, repulsion force is generated between impeller 10 and diaphragm 6 and it acts as hydrodynamic pressure.

In this manner, owing to the hydrodynamic bearing effect produced between impeller 10 and the plurality of grooves for hydrodynamic bearing 21, impeller 10 moves away from diaphragm 6 and rotates without contacting. Accordingly, a blood flow path is secured between impeller 10 and diaphragm 6, thus preventing occurrence of blood accumulation therebetween and the resultant thrombus. Further, in a normal state, grooves for hydrodynamic bearing 21 perform a stirring function between impeller 10 and diaphragm 6, thus preventing occurrence of partial blood accumulation therebetween.

Instead of providing grooves for hydrodynamic bearing 21 in diaphragm 6, grooves for hydrodynamic bearing 21 may be provided in a surface of shroud 12 of impeller 10.

It is preferable that a corner portion of groove for hydrodynamic hearing 21 be rounded to have R of at least 0.05 mm. As a result, occurrence of hemolysis can further be lessened.

Figure 7:
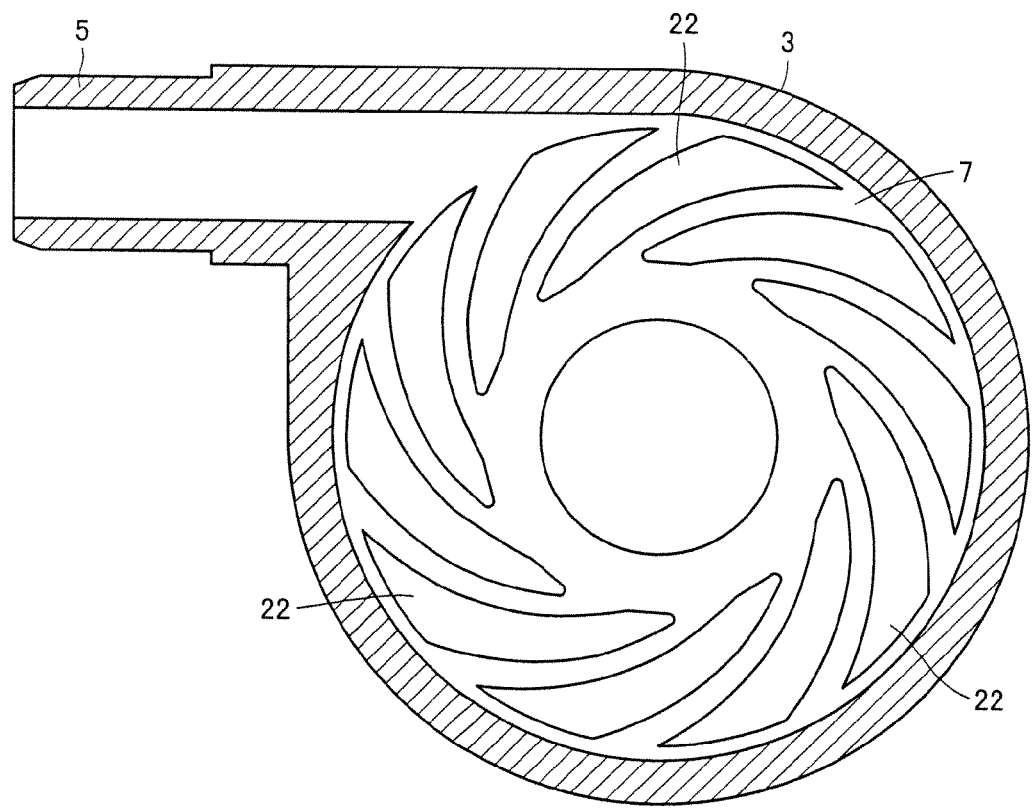
FIG. 7 is a cross-sectional view showing the state where the impeller has been removed from a cross-sectional view along the line VII-VII in FIG. 3.

As with the plurality of grooves for hydrodynamic bearing 21, as shown in FIG. 7, the plurality of grooves for hydrodynamic bearing 22 are formed with a size corresponding to shroud 11 of impeller 10. Each of grooves for hydrodynamic bearing 22 has one end on the edge (circumference) of the circular portion slightly distant from the center of the inner wall of blood chamber 7, and extends spirally (in other words, in a curved manner) toward the portion near the outer edge of the inner wall of blood chamber 7 such that groove for hydrodynamic bearing 22 gradually increases in width. The plurality of grooves for hydrodynamic bearing 22 have substantially the same shape and they are arranged at substantially regular intervals. Groove for hydrodynamic bearing 22 is a concave portion and it preferably has a depth of about 0.005 to 0.4 mm. It is preferable that about 6 to 36 grooves for hydrodynamic bearing 22 be provided. In FIG. 7, ten grooves for hydrodynamic bearing 22 are equiangularly arranged with respect to the central axis of impeller 10.

Owing to the hydrodynamic hearing effect produced between impeller 10 and the plurality of grooves for hydrodynamic bearing 22, impeller 10 moves away from the inner wall of blood chamber 7 and rotates without contacting. In addition, when pump unit 1 is subjected to external impact or when the hydrodynamic pressure generated by grooves for hydrodynamic bearing 21 becomes excessive, impeller 10 can be prevented from being in close contact with the inner wall of blood chamber 7. The hydrodynamic pressure generated by grooves for hydrodynamic bearing 21 may be different from the hydrodynamic pressure generated by grooves for hydrodynamic hearing 22.

Grooves for hydrodynamic bearing 22 may be provided in a surface of shroud 11 of impeller 10, rather than on the inner surface side of blood chamber 7. It is preferable that a corner portion of groove for hydrodynamic bearing 22 be rounded to have R of at least 0.05 mm. As a result, occurrence of hemolysis can further be lessened.

It is preferable that impeller 10 rotate in a state where a gap between shroud 12 of impeller 10 and diaphragm 6 is substantially equal to a gap between shroud 11 of impeller 10 and the inner wall of blood chamber 7. If one of the gaps becomes narrower due to serious disturbance such as hydrodynamic force acting on impeller 10, it is preferable that grooves for hydrodynamic bearing 21 and 22 have different shapes, so that the hydrodynamic pressure generated by the grooves for hydrodynamic bearing on the narrower side becomes higher than the hydrodynamic pressure generated by the other grooves for hydrodynamic bearing to make the gaps substantially equal to each other.

While both of grooves for hydrodynamic bearing 21 and 22 have the inward spiral groove shape in FIGS. 6 and 7, grooves for hydrodynamic bearing 21 and 22 having another shape may be used. Nevertheless, for blood circulation, it is preferable to employ grooves for hydrodynamic bearing 21 and 22 having the inward spiral groove shape that allows smooth flow of blood.

Figure 11:
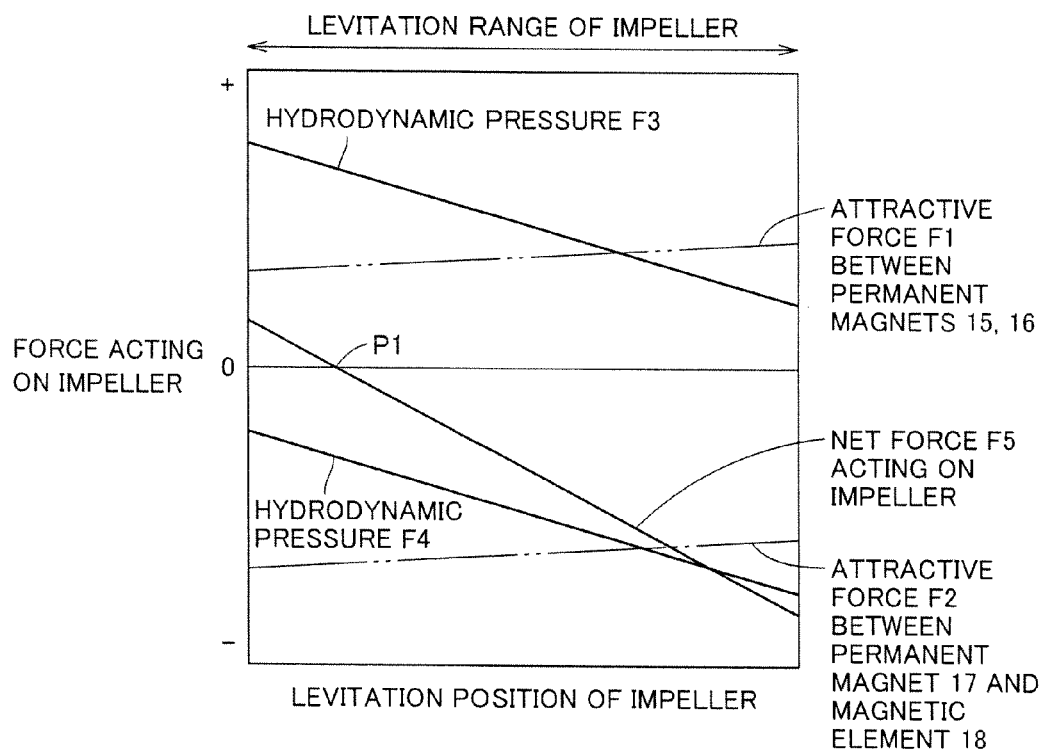
FIG. 11 is a diagram showing relation between a levitation position of the impeller and force acting on the impeller.

FIG. 11 is a diagram showing forces acting on impeller 10 when magnitude of a resultant force of an attractive force F1 between permanent magnets 15a, 15b and permanent magnets 16a, 16b (abbreviated as between permanent magnets 15 and 16 in FIG. 11) and an attractive force F2 between permanent magnet 17 and magnetic element 18 is adjusted to zero at a position P1 other than a central position of the movable range of impeller 10 in blood chamber 7. The rotation speed of impeller 10 is kept at a rated value.

Namely, it is assumed that attractive force F1 between permanent magnets 15a, 15b and permanent magnets 16a, 16b is set to be smaller than attractive force F2 between permanent magnet 17 and magnetic element 18 and a levitation position of impeller 10 where their resultant force becomes zero is on the diaphragm 6 side relative to the center of the movable range of the impeller. Grooves for hydrodynamic bearing 21, 22 have the same shape.

A horizontal axis of FIG. 11 represents a position of impeller 10 (the left side in the figure being the diaphragm 6 side) and a vertical axis represents forces acting on impeller 10. Force acting on impeller 10 toward the diaphragm 6 side is expressed as a negative acting force. As the forces acting on impeller 10, attractive force F1 between permanent magnets 15a, 15b and permanent magnets 16a, 16b, attractive force F2 between permanent magnet 17 and magnetic element 18, a hydrodynamic pressure F3 generated by grooves for hydrodynamic bearing 21, a hydrodynamic pressure F4 generated by grooves for hydrodynamic bearing 22, and "net force F5 acting on impeller," which is their resultant force, are illustrated.

As can be seen in FIG. 11, at a position where net force F5 acting on impeller 10 becomes zero, the levitation position of impeller 10 is significantly deviated from the central position of the movable range of impeller 10. As a result, a distance between rotating impeller 10 and diaphragm 6 becomes narrower, and impeller 10 comes in contact with diaphragm 6 even by the action of small disturbance force on impeller 10.

Figure 12:
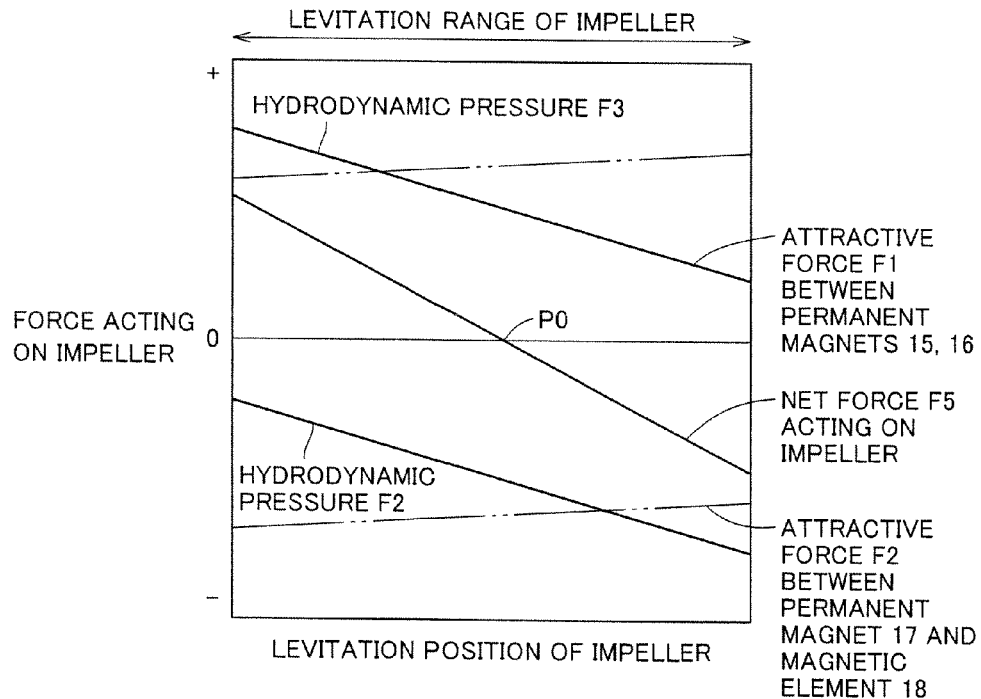
FIG. 12 is another diagram showing relation between a levitation position of the impeller and force acting on the impeller.

In contrast, FIG. 12 is a diagram showing forces acting on impeller 10 when magnitude of the resultant force of attractive force F1 between permanent magnets 15a, 15b and permanent magnets 16a, 16b and attractive force F2 between permanent magnet 17 and magnetic element 18 is adjusted to zero at a central position P0 of the movable range of impeller 10 in blood chamber 7. The rotation speed of impeller 10 is kept at the rated value also in this case.

Namely, attractive force F1 between permanent magnets 15a, 15b and permanent magnets 16a, 16b and attractive force F2 between permanent magnet 17 and magnetic element 18 are set to be substantially equal to each other. In addition, grooves for hydrodynamic bearing 21, 22 have the same shape. In this case, since net force F5 acting on impeller 10 is zero at the center of the movable range, impeller 10 is levitated at the central position when disturbance force is not acting on impeller 10.

As such, a levitation position of impeller 10 is determined by balance among attractive force F1 between permanent magnets 15a, 15b and permanent magnets 16a, 16b, attractive force F2 between permanent magnet 17 and magnetic element 18, and hydrodynamic pressures F3, F4 generated by grooves for hydrodynamic bearing 21, 22 during rotation of impeller 10. By making F1 and F2 substantially equal to each other and by forming grooves for hydrodynamic bearing 21, 22 in the same shape, impeller 10 can be levitated substantially in a central portion of blood chamber 7 during rotation of impeller 10. Since impeller 10 has such a shape that vanes are formed between two discs as shown in FIGS. 3 and 4, two surfaces facing the inner wall of housing 2 can be formed to have the same shape and the same dimensions. Therefore, it is possible to provide grooves for hydrodynamic bearing 21, 22 having a function to generate substantially the same hydrodynamic pressure on both sides of impeller 10.

In this case, impeller 10 is levitated at the central position of blood chamber 7 and thus held at a position farthest from the inner wall of housing 2. As a result, even if the levitation position of impeller 10 is changed due to application of disturbance force to levitated impeller 10, the possibility that impeller 10 is brought into contact with the inner wall of housing 2 is lowered, thus also lowering the possibility of occurrence of thrombus and hemolysis resulting from such contact.

While grooves for hydrodynamic bearing 21, 22 have the same shape in the examples shown in FIGS. 11 and 12, grooves for hydrodynamic bearing 21 may be different in shape and hydrodynamic pressure generating function from grooves for hydrodynamic bearing 22. For example, when disturbance acts on impeller 10 always in one direction due to hydrodynamic force or the like during pumping, performance of a groove for hydrodynamic bearing in the disturbance direction may be made higher than performance of the other groove for hydrodynamic hearing, thereby levitating and rotating impeller 10 at the central position of housing 2. As a result, the probability of contact between impeller 10 and housing 2 can be lowered, thereby attaining stable levitation performance of impeller 10.

Furthermore, when an absolute value of a negative axial supporting rigidity value of impeller 10 which is constituted of attractive force F1 between permanent magnets 15a, 15b and permanent magnets 16a, 16b and attractive force F2 between permanent magnet 17 and magnetic element 18 is expressed as Ka, an absolute value of a positive radial rigidity value is expressed as Kr, and an absolute value of a positive rigidity value obtained by two grooves for hydrodynamic bearing 21, 22 in a normal rotation speed range where impeller 10 rotates is expressed as Kg, it is preferable that relation of Kg>Ka+Kr be satisfied.

Specifically, when absolute value Ka of the negative axial rigidity value is 20000 N/m and absolute value Kr of the positive radial rigidity value is 10000 N/m, absolute value Kg of the positive rigidity value obtained by two grooves for hydrodynamic bearing 21, 22 in a rotation speed region where impeller 10 normally rotates is set to a value higher than 30000 N/m.

The axial supporting rigidity for impeller 10 is a value obtained by subtracting negative rigidity due to the attractive force between the magnetic elements and the like from rigidity resulting from the hydrodynamic pressure generated by grooves for hydrodynamic hearing 21, 22. Thus, by satisfying relation of Kg>Ka+Kr, the axial supporting rigidity for impeller 10 can be made higher than the radial supporting rigidity. With such setting, movement of impeller 10 can be suppressed more in the axial direction than in the radial direction when disturbance force acts on impeller 10, thereby avoiding mechanical contact between impeller 10 and housing 2 in a portion where grooves for hydrodynamic bearing 21 are formed.

In particular, since grooves for hydrodynamic bearing 21, 22 are provided as concave portions in planar surfaces as shown in FIGS. 3, 6 and 7, mechanical contact between housing 2 and impeller 10 in these portions during rotation of impeller 10 may result in damage to one or both of a surface of impeller 10 and a surface of the inner wall of housing 2 (projections and recesses in the surfaces), and blood passage through this portion may cause occurrence of thrombus and hemolysis. In order to prevent mechanical contact at grooves for hydrodynamic bearing 21, 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15a, 15b and permanent magnets 16a, 16b and attractive force F2 between permanent magnet 17 and magnetic element 18 is expressed as Kr (N/m), the mass of impeller 10 is expressed as m (kg), and the rotation speed of the impeller is expressed as ω(rad/s), it is preferable that relation of $\omega<(Kr/m)^{0.5}$ be satisfied.

Specifically, when the mass of impeller 10 is 0.03 kg and the radial rigidity value is 2000 N/m, the maximum rotation speed of impeller 10 is set to 258 rad/s (2465 rpm) or lower. Conversely, when the maximum rotation speed of impeller 10 is set to 366 rad/s (3500 rpm), the radial rigidity is set to 5018 N/m or higher.

It is further preferable to set the maximum rotation speed of impeller 10 to 80% or lower of this ω. Specifically, when the mass of impeller 10 is 0.03 kg and the radial rigidity value is 2000 N/m, the maximum rotation speed is set to 206.4 rad/s (1971 rpm) or lower. Conversely, when it is desired to set the maximum rotation speed of impeller 10 to 366 rad/s (3500 rpm), the radial rigidity value is set to 6279 N/m or higher. By thus setting the maximum rotation speed of impeller 10, contact between rotating impeller 10 and housing 2 can be suppressed.

Figure 13:
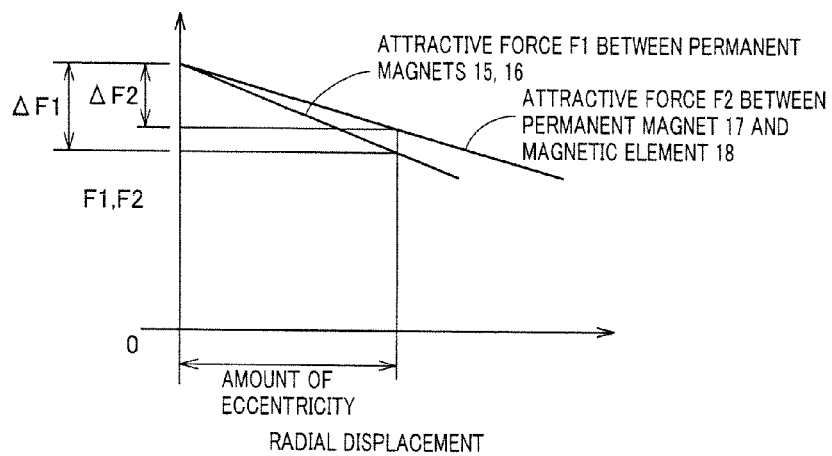
FIG. 13 is a diagram showing relation between an amount of eccentricity in a radial direction of the impeller and force acting on the impeller.

In addition, as shown in FIG. 13, attractive force F1 between permanent magnets 15a, 15b and permanent magnets 16a, 16b (abbreviated as between permanent magnets 15 and 16 in FIG. 13) decreases with movement of impeller 10 in the radial direction. Similarly, attractive force F2 between permanent magnet 17 and magnetic element 18 decreases with movement of impeller 10 in the radial direction.

During a desired pump operation, impeller 10 is eccentric in the radial direction. Therefore, when an amount of change ΔF1 in attractive force F1 with respect to an amount of eccentricity of impeller 10 is different from an amount of change ΔF2 in attractive force F2 with respect to the amount of eccentricity of impeller 10, a levitation position of impeller 10 at that eccentric position is displaced from the central position in blood chamber 7. Therefore, if any one gap of the gap between impeller 10 and the inner wall of blood chamber 7 and the gap between impeller 10 and diaphragm 6 becomes narrow, impeller 10 is brought into contact with the inner wall of blood chamber 7 or with diaphragm 6 even by action of small disturbance on impeller 10.

On the other hand, in a case where amount of change ΔF1 in attractive force F1 is equal to amount of change ΔF2 in attractive force F2, even though impeller 10 is eccentric in the radial direction, a levitation position of impeller 10 is maintained at a central position in blood chamber 7. Therefore, even when disturbance acts on impeller 10, it is less likely that impeller 10 comes in contact with the inner wall of blood chamber 7 or diaphragm 6. Then, in this first embodiment, by adjusting a phase of a current to be fed to coil 20, relation of ΔF1≈ΔF2 is satisfied. Thus, even when impeller 10 is eccentric in the radial direction, a levitation position of impeller 10 in the axial direction is kept at the central position in blood chamber 7.

Figure 14:
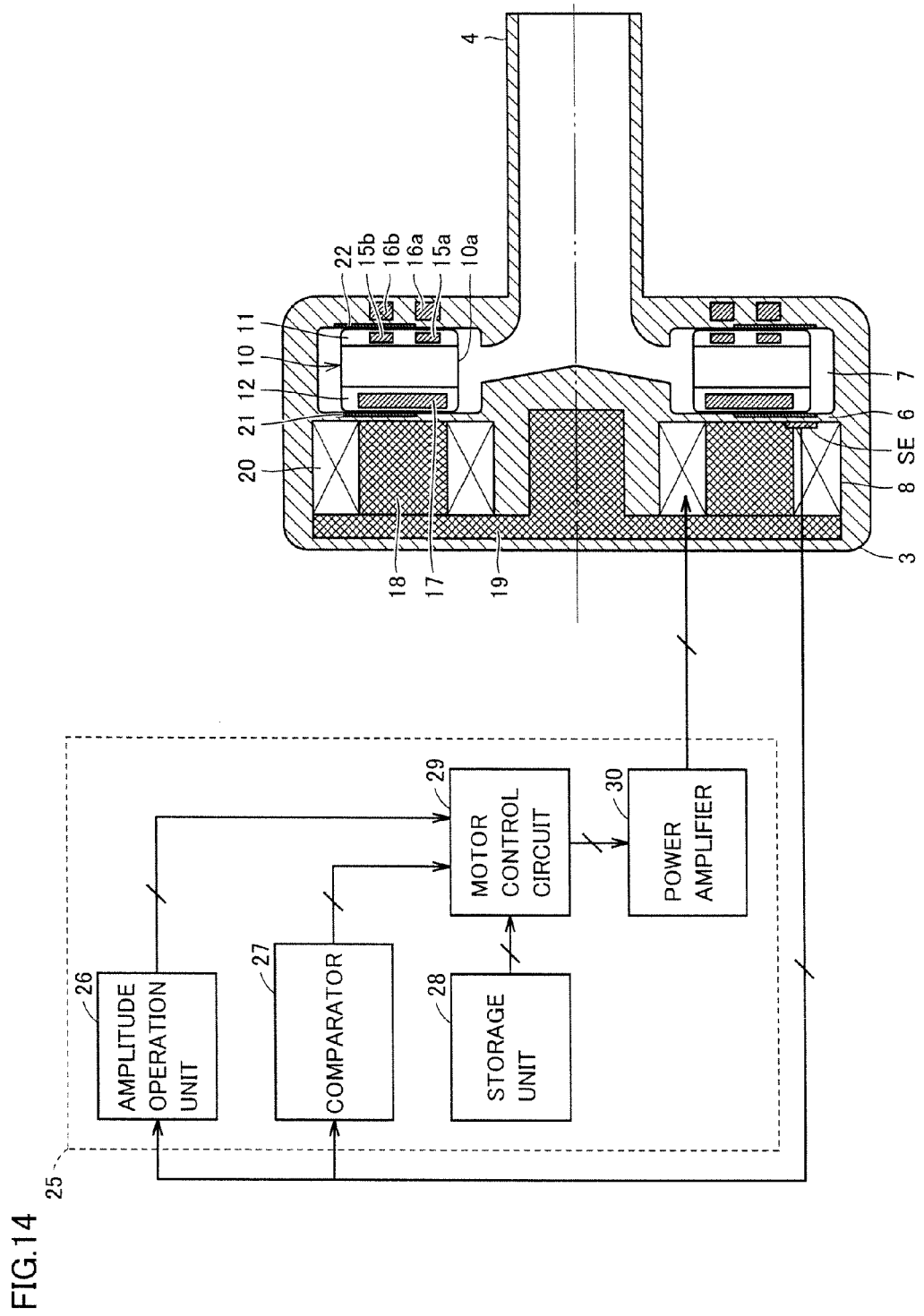
FIG. 14 is a block diagram showing a configuration of a controller for controlling the pump unit shown in FIGS. 1 to 8.

FIG. 14 is a block diagram showing a configuration of a controller 25 for controlling pump unit 1. In FIG. 14, controller 25 includes an amplitude operation unit 26, a comparator 27, a storage unit 28, a motor control circuit 29, and a power amplifier 30. Amplitude operation unit 26 operates an amplitude of an output signal from magnetic sensor SE, operates a levitation position of impeller 10 based on the amplitude, and provides a signal indicating the levitation position of impeller 10 to motor control circuit 29. Comparator 27 compares magnitude of output signals from three magnetic sensors SE and a reference voltage, detects a status of rotation of permanent magnet 17 based on a result of comparison, and provides a rotational drive signal indicating a status of rotation of permanent magnet 17 to motor control circuit 29. Storage unit 28 stores waveforms of output signals from amplitude operation unit 26 and comparator 27 while impeller 10 rotates at the central position in the movable range at a prescribed rotation speed.

Motor control circuit 29 outputs three-phase control signals in the power distribution system shifted by 120 degrees, for example, such that waveforms of the output signals from amplitude operation unit 26 and comparator 27 match waveforms stored in storage unit 28. Power amplifier 27 amplifies the three-phase control signals from motor control circuit 29 and generates three-phase voltages VU, VV and VW shown in FIG. 10. Three-phase voltages VU, VV and VW are applied to first to third coils 20 described with reference to FIGS. 8 to 10, respectively. As a result, three-phase AC currents flow through first to third coils 20 and impeller 10 rotates at a prescribed rotation speed at the central position of the movable range.

As impeller 10 is eccentric in the radial direction, attractive forces F1, F2 decrease, however, a load current is increased in order to perform a desired pump operation, and hence attractive force F2 increases. Adjustment of attractive force F2 is made by adjusting a phase of a current fed to coil 20.

Namely, when a phase difference between three-phase voltages VU, VV, VW and the output signals from three magnetic sensors SE is at a prescribed value, efficiency is maximized. As phases of three-phase voltages VU, VV, VW are advanced with respect to phases of the output signals from three magnetic sensors SE, attractive force F2 between permanent magnet 17 and magnetic element 18 decreases. In contrast, as phases of three-phase voltages VU, VV, VW are delayed with respect to phases of the output signals from three magnetic sensors SE, attractive force F2 between permanent magnet 17 and magnetic element 18 increases.

Therefore, when impeller 10 is eccentric in the radial direction and the levitation position of impeller 10 in the axial direction is displaced from the central position in blood chamber 7, the levitation position of impeller 10 can be returned to the central position in blood chamber 7 by adjusting phases of three-phase voltages VU, VV, VW, that is, phases of three-phase AC currents fed to coil 20, in accordance with the levitation position of impeller 10.

It is noted that an amount of change in attractive force F2 in connection with phase adjustment of three-phase voltages VU, VV, VW is approximately ±1 N in the present first embodiment, although it is different depending on a dimension of an apparatus or an output. On the other hand, an amount of change in attractive force F1 between permanent magnets 15a, 15b and permanent magnets 16a, 16b with fluctuation in a position of impeller 10 is not greater than 1 N.

Therefore, relation of F1 F2 can be satisfied by adjusting phases of three-phase voltages VU, VV, VW.

In this first embodiment, attractive force between permanent magnets 15a, 15b and permanent magnets 16a, 16b is balanced with attractive force between a plurality of permanent magnets 50 and a plurality of permanent magnets 51 and grooves for hydrodynamic bearing 21, 22 are provided. Therefore, rigidity for supporting impeller 10 in the axial direction can be increased. In addition, since two pairs of permanent magnets 15a, 16a and permanent magnets 15b, 16b are provided in the radial direction of impeller 10, rigidity for supporting impeller 10 in the radial direction can be increased as compared with a case where only a pair of permanent magnets is provided in the radial direction of impeller 10. Further, since amount of change ΔF1 in attractive force F1 between permanent magnets 15a, 15b and permanent magnets 16a, 16b and amount of change ΔF2 in attractive force F2 between permanent magnet 17 and magnetic element 18 when impeller 10 is eccentric are made substantially equal to each other, rigidity for supporting impeller 10 in the axial direction can be increased. Therefore, mechanical contact between impeller 10 and housing 2 can be lessened and occurrence of hemolysis or thrombus can be prevented.

It is noted that a diamond-like carbon (DLC) coating may be formed on at least one of the surface of the inner wall of blood chamber 7 and the surface of diaphragm 6, and the surface of impeller 10. As a result, frictional force between impeller 10, and the inner wall of blood chamber 7 and diaphragm 6 can be lowered to smoothly activate the impeller to rotate. A fluorine-based resin coating, a paraxylylene-based resin coating or the like may be formed instead of the diamond-like carbon coating.

Figure 15:
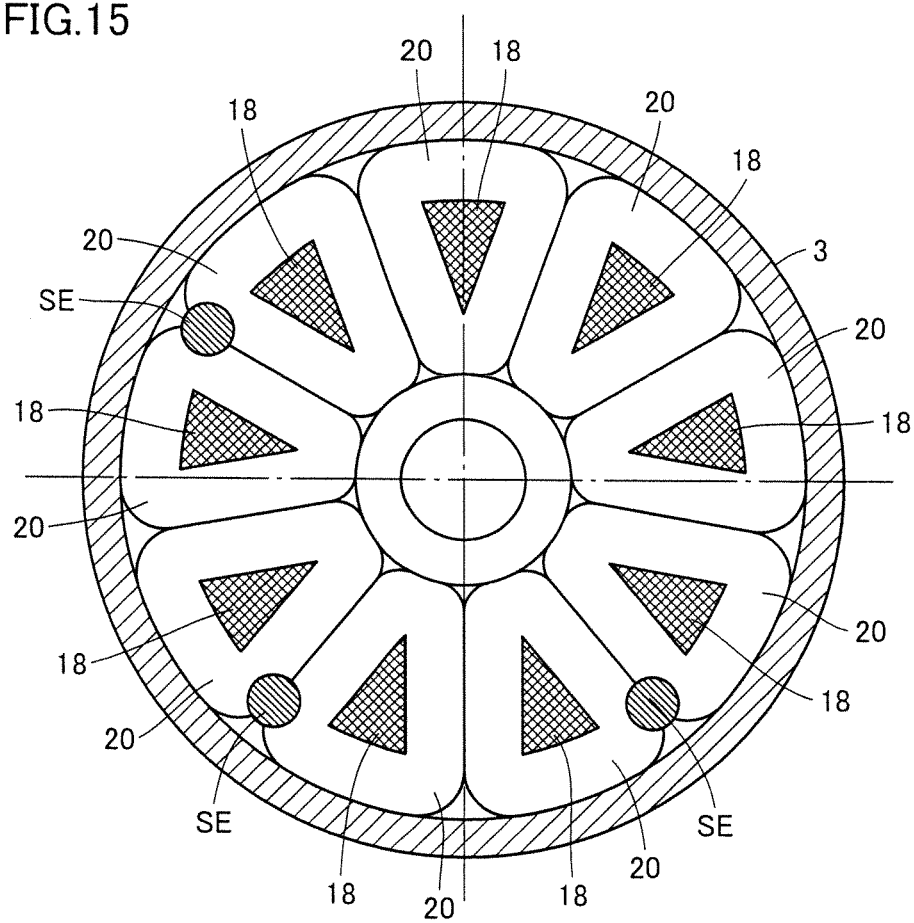
FIG. 15 is a cross-sectional view showing a modification of this first embodiment.

FIG. 15 is a cross-sectional view showing a modification of this first embodiment, which is compared to FIG. 8. In this modification, nine coils 20 are divided into three groups each including three coils, and voltages VU, VV and VW in FIG. 10 are applied to first to third coils 20 of each group, respectively. First magnetic sensor SE is arranged between first and second coils 20 of the first group, Second magnetic sensor SE is arranged between third coil 20 of the first group and first coil 20 of the second group. Third magnetic sensor SE is arranged between second and third coils 20 of the second group. Accordingly, an electrical angle between first to third magnetic sensors SE is maintained at 120 degrees. Based on output signals from first to third magnetic sensors SE, three-phase control signals can be generated and an axial position of impeller 10 can be detected. Further, a mechanical angle between first to third magnetic sensors SE is each 80 degrees, and hence a levitation posture of rotating impeller 10 can also be detected.

Figure 16:
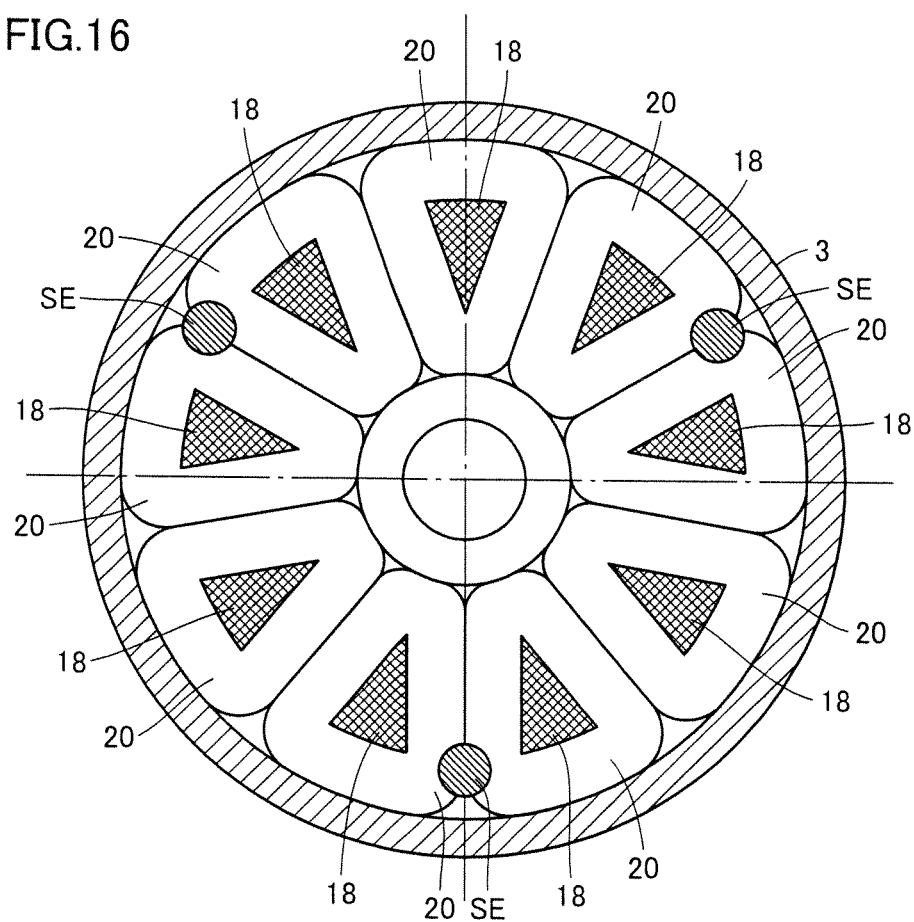
FIG. 16 is a cross-sectional view showing another modification of this first embodiment.

FIG. 16 is a cross-sectional view showing another modification of this first embodiment, which is compared to FIG. 8. In this modification, nine coils 20 are divided into three groups each including three coils, and three magnetic sensors SE are arranged between the three groups of coils, respectively. Accordingly, a mechanical angle between three magnetic sensors SE is 120 degrees, allowing easy operation of a levitation posture of rotating impeller 10. Timing for feeding a current through nine coils 20 is operated based on an output signal from any one of three magnetic sensors SE.

Figure 17:
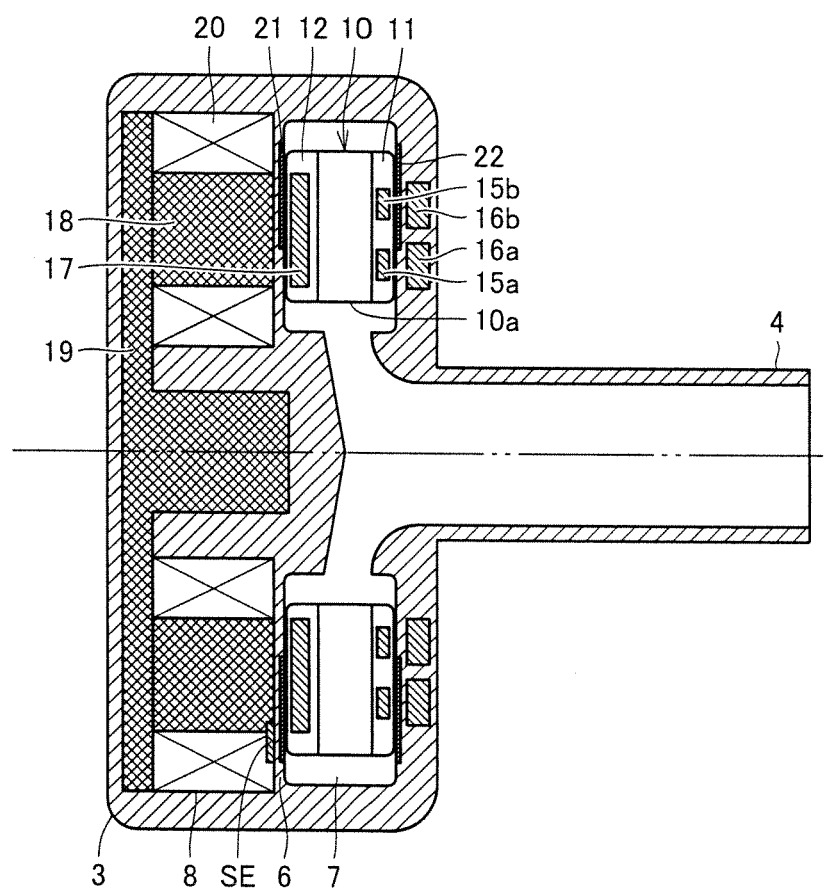
FIG. 17 is a cross-sectional view showing yet another modification of the first embodiment.

When rigidity derived from hydrodynamic pressure generated by grooves for hydrodynamic bearing 21, 22 is greater than a negative rigidity value of impeller 10 in the axial direction constituted of attractive force F1 between permanent magnets 15a, 15b and permanent magnets 16a, 16b and attractive force F2 between permanent magnet 17 and magnetic element 18, impeller 10 and housing 2 do not come in contact with each other. Therefore, this negative rigidity value is preferably minimized. In order to suppress this negative rigidity value to be small, preferably, opposing surfaces of permanent magnets 15a and 16a are different in size and opposing surfaces of permanent magnets 15b and 16b are different in size. For example, as shown in FIG. 17, by making permanent magnets 15a, 15b smaller than permanent magnets 16a, 16b, a rate of change in attractive force which varies with a distance between the magnets, that is, the negative rigidity, can be suppressed to be low, thereby preventing lowering in rigidity for supporting the impeller.

Figure 18:
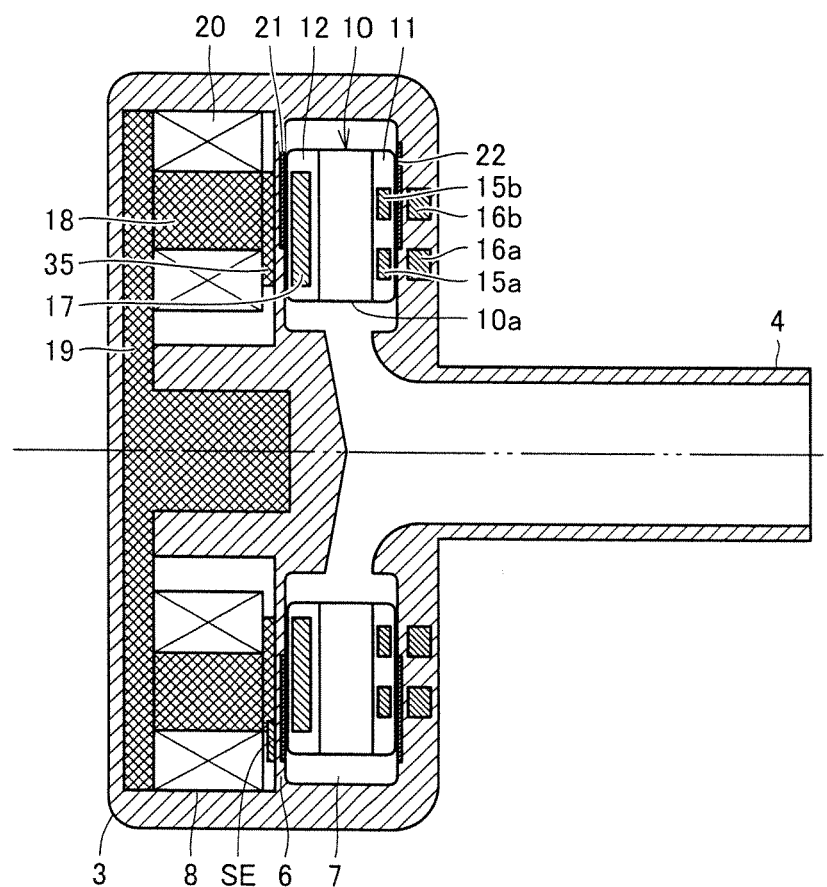
FIG. 18 is a cross-sectional view showing yet another modification of the first embodiment.

FIG. 18 is a cross-sectional view showing yet another modification of this first embodiment, which is compared to FIG. 3. Referring to FIG. 18, in this modification, a magnetic element 35 is provided on a tip surface of each magnetic element 18 facing permanent magnet 17. A surface of magnetic element 35 facing permanent magnet 17 has an area larger than an area of the tip surface of magnetic element 18. In this modification, attractive force of magnetic elements 18 and 35 on permanent magnet 17 can be increased, thus increasing energy efficiency when impeller 10 is driven to rotate.

Figure 19:
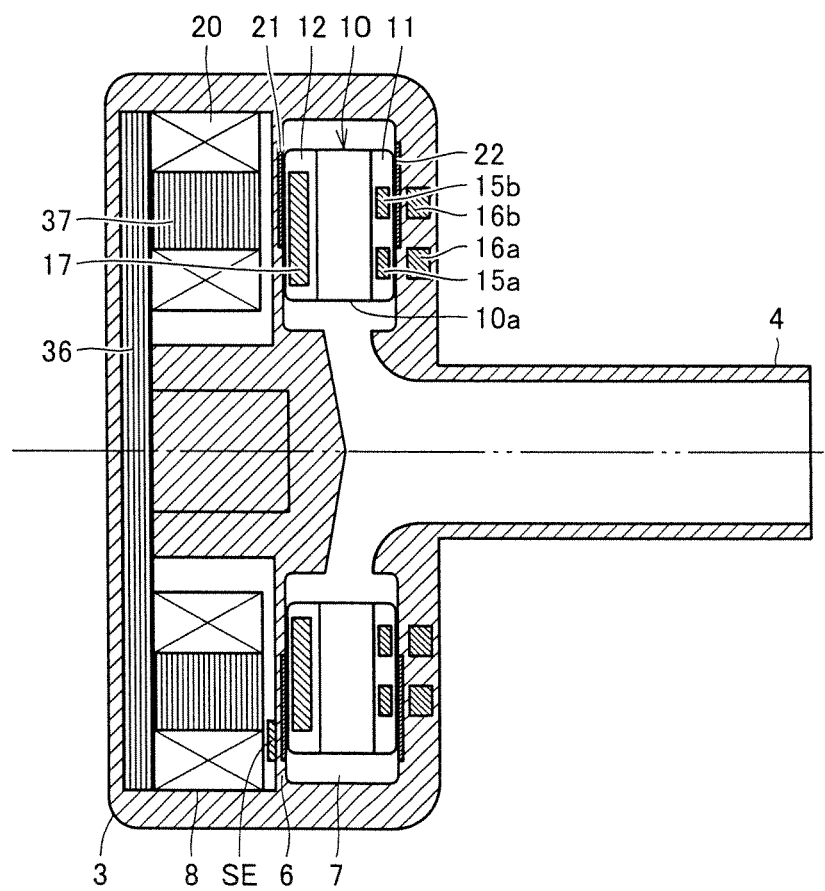
FIG. 19 is a cross-sectional view showing yet another modification of the first embodiment.

FIG. 19 is a cross-sectional view showing yet another modification of this first embodiment, which is compared to FIG. 3. Referring to FIG. 19, in this modification, yoke 19 is replaced with a yoke 36 and magnetic element 18 is replaced with a magnetic element 37. Yoke 36 and magnetic element 37 each include a plurality of steel plates stacked in a length direction of a rotation axis of impeller 10. In this modification, eddy current loss that occurs in yoke 36 and magnetic element 37 can be reduced, thus increasing energy efficiency when impeller 10 is driven to rotate.

Figure 20:
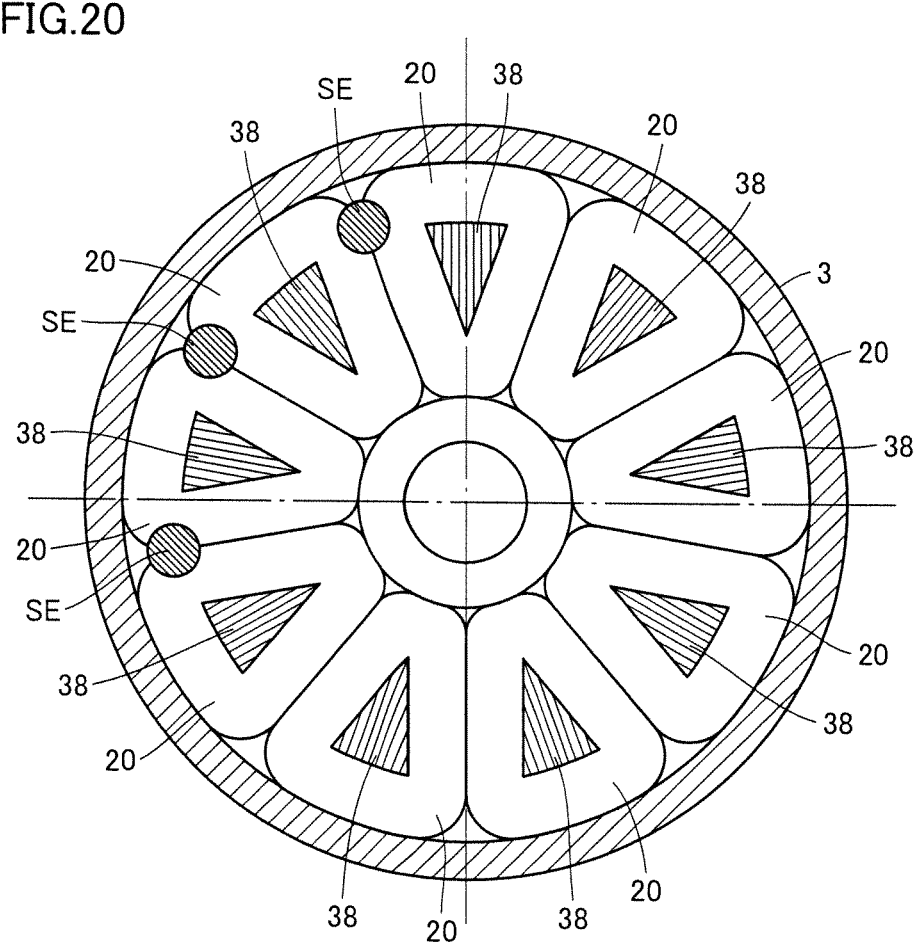
FIG. 20 is a cross-sectional view showing yet another modification of the first embodiment.
Figure 21:
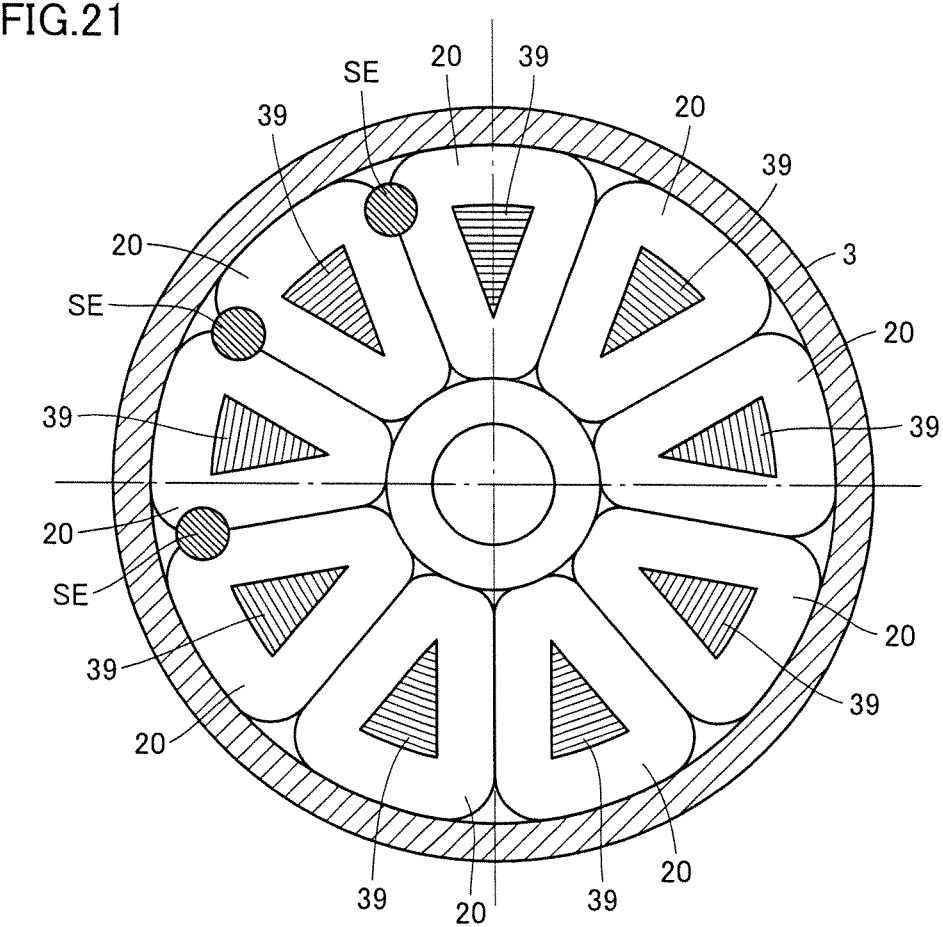
FIG. 21 is a cross-sectional view showing yet another modification of the first embodiment.

Alternatively, as shown in FIG. 20, a magnetic element 32 may be replaced with a magnetic element 38 including a plurality of steel plates stacked in a rotation direction of impeller 10. Alternatively, as shown in FIG. 21, magnetic element 32 may be replaced with a magnetic element 39 including a plurality of steel plates stacked in a radial direction of impeller 10. The same effect as in the modification in FIG. 19 can be obtained also in these cases.

Alternatively, each of yoke 19 and magnetic element 18 in FIG. 3 may be made of powders of pure iron, soft iron or ferrosilicon. In this case, iron loss in yoke 19 and magnetic element 18 can be reduced, thus increasing energy efficiency when impeller 10 is driven to rotate.

Figure 22:
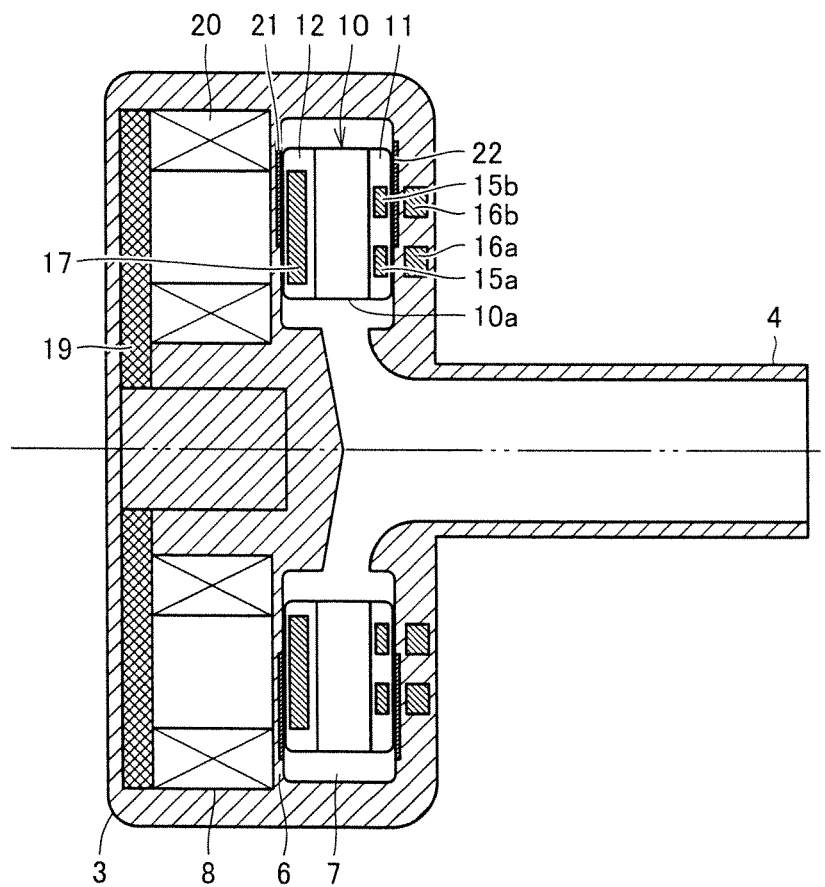
FIG. 22 is a cross-sectional view showing yet another modification of the first embodiment.

FIG. 22 is a cross-sectional view showing yet another modification of this first embodiment, which is compared to FIG. 3. Referring to FIG. 22, in this modification, magnetic element 18 has been removed. In this modification, magnitude of a resultant force of attractive force F1 between permanent magnets 15a, 15h and permanent magnets 16a, 16b and attractive force F2 between permanent magnet 17 and yoke 19 is adjusted to zero at position P0 in the movable range of impeller 10 in blood chamber 7. The same effect as in the first embodiment can be obtained also in this modification.

Figure 23:
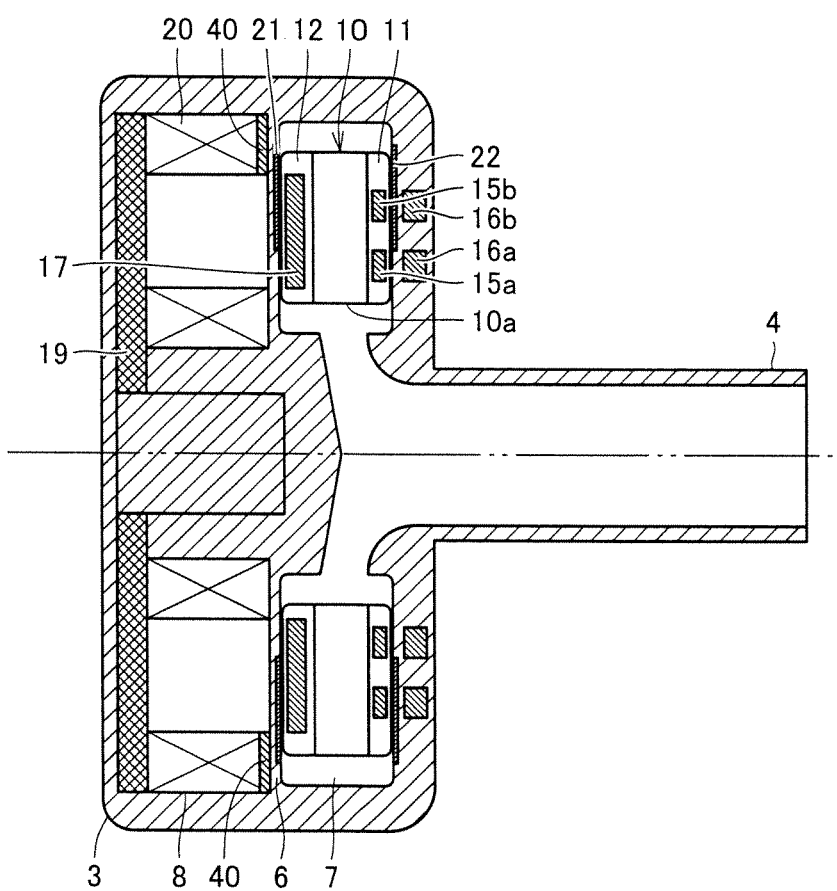
FIG. 23 is a cross-sectional view showing yet another modification of the first embodiment.

When attractive force F2 between permanent magnet 17 and yoke 19 is smaller than attractive force F1 between permanent magnets 15a, 15b and permanent magnets 16a, 16b, as shown in FIG. 23, a magnetic element 40 is arranged at a position different from that of coils 20 and attractive force F3 of magnetic element 40 and permanent magnet 17 is added so that attractive force F1 is balanced with attractive force F2+F3 substantially at the center in the movable range of impeller 10. Here, magnetic element 40 may be a permanent magnet.

Figure 24:
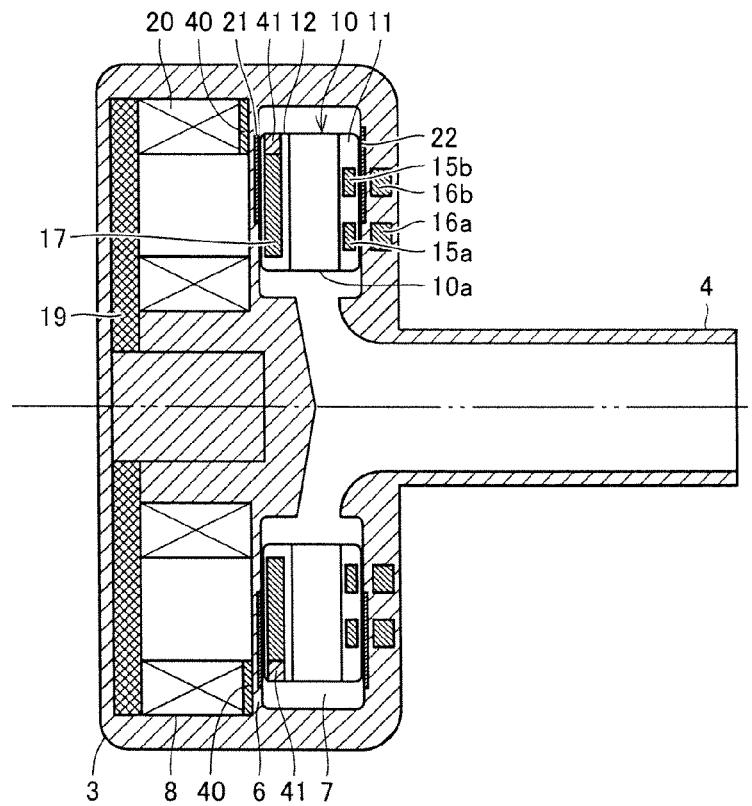
FIG. 24 is a cross-sectional view showing yet another modification of the first embodiment.

Alternatively, as shown in FIG. 24, a permanent magnet 41 may be arranged at a position in impeller 10 facing magnetic element 40 and attractive force F4 between magnetic element 40 and permanent magnet 41 may be added so that attractive force F1 is balanced with attractive force F2+F3+F4 substantially at the center in the movable range of impeller 10. Here, magnetic element 41 may be a permanent magnet. Alternatively, when magnetic element 40 is a permanent magnet, permanent magnet 41 may be a magnetic element.

Figure 25:
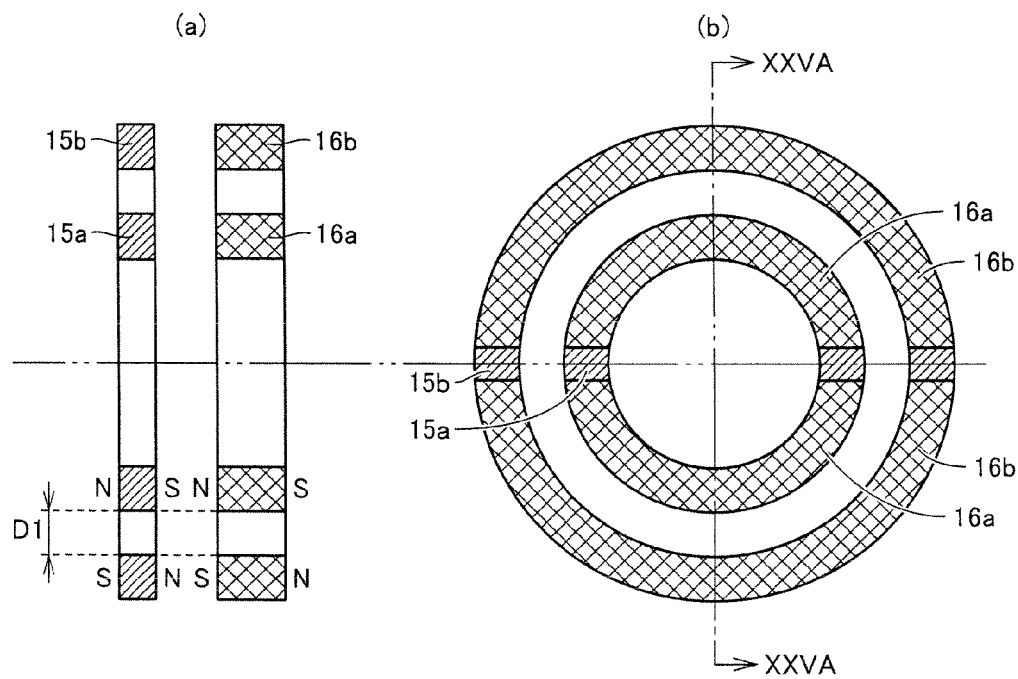
FIG. 25 is a diagram showing yet another modification of the first embodiment.

FIGS. 25 (a) and (b) are cross-sectional views showing yet another modification of this first embodiment, which are compared to FIGS. 5 (a) and (b). FIG. 22 (a) is a cross-sectional view along the line XXVA-XXVA in FIG. 22 (b). In this modification, the N pole of permanent magnet 15a and the N pole of permanent magnet 15b are provided in directions opposite to each other, and the N pole of permanent magnet 16a and the N pole of permanent magnet 16b are provided in directions opposite to each other. The S pole of permanent magnet 15a faces the N pole of permanent magnet 16a and the N pole of permanent magnet 15b faces the S pole of permanent magnet 16b. The same effect as in the first embodiment can be obtained also in this modification.

Though a case where the invention of the subject application is applied to a centrifugal blood pump apparatus including magnetic sensor SE has been described in this first embodiment, the invention of the subject application is applicable also to a sensorless drive type centrifugal blood pump apparatus without including magnetic sensor SE. In sensorless drive, phase information is found from a counterelectromotive force waveform and a current waveform generated in coil 20 as permanent magnet 17 rotates or change in inductance in coil 20, and a phase of a current fed to coil 20 is adjusted based on the phase information. Alternatively, in a case where vector control is employed, magnitude of a d-axis current Id (excitation current) is varied while a q-axis current Iq (torque current) is maintained, so that an effect the same as that of phase adjustment can be obtained.

[Second Embodiment]

Figure 26:
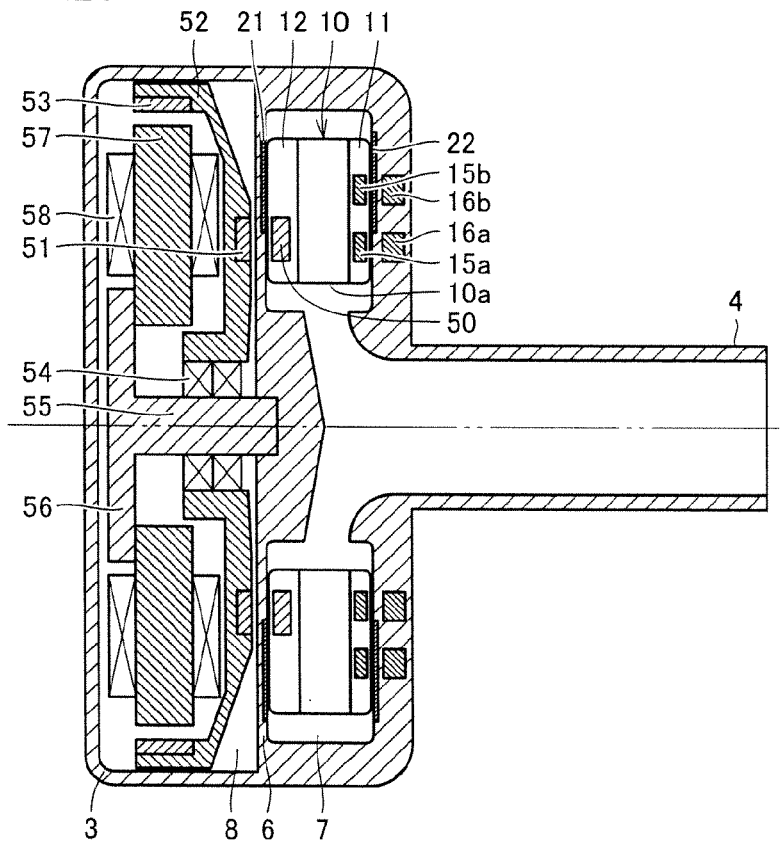
FIG. 26 is a cross-sectional view showing a structure of a pump unit of a centrifugal blood pump apparatus according to a second embodiment of the present invention.

FIG. 26 is a cross-sectional view showing a structure of a pump unit of a centrifugal blood pump apparatus according to a second embodiment of the present invention, which is compared to FIG. 3. In FIG. 26, in this pump unit, a plurality of (e.g. eight) permanent magnets 50 instead of the plurality of permanent magnets 17 are embedded in shroud 12 of impeller 10. The plurality of permanent magnets 50 are arranged at regular angular intervals along the same circle. In motor chamber 8, a plurality of (e.g., eight) permanent magnets 51 for attracting the plurality of permanent magnets 50 are provided. The plurality of permanent magnets 51 are arranged at regular angular intervals along the same circle to face the plurality of permanent magnets 50 in impeller 10.

The plurality of permanent magnets 51 are provided in a surface of a bowl-shaped rotor 52. A plurality of (e.g., eight) permanent magnets 53 are provided at regular angular intervals on an inner side of a circumference of rotor 52. The plurality of permanent magnets 53 are arranged at regular angular intervals along the same circle such that adjacent magnetic polarities thereof are different from each other. In other words, permanent magnet 53 having the N-pole toward the inside of rotor 52 and permanent magnet 53 having the S-pole toward the inside of rotor 52 are alternately arranged at regular angular intervals along the same circle.

A central portion of rotor 52 is rotatably supported by a central axis 55 with a bearing 54 being interposed, and rotor 52 is rotatably provided along diaphragm 6. Central axis 55 is provided to stand in a center of a disc-shaped yoke 56. A plurality of (e.g., nine) magnetic elements 57 are provided at regular angular intervals around central axis 55 on the surface of yoke 56. Tip ends of the plurality of magnetic elements 57 are arranged along the same circle, as facing the plurality of permanent magnets 53 in rotor 52. A coil 58 is wound around each magnetic element 57. The plurality of permanent magnets 53, the plurality of magnetic elements 57, and a plurality of coils 58 constitute a motor for rotating rotor 52.

Voltages are applied to nine coils 58 in a power distribution system shifted by 120 degrees, for example. Namely, nine coils 58 are divided into groups each including three coils. Voltages VU, VV and VW shown in FIG. 9 are applied to first to third coils 58 of each group, respectively. Thus, rotating magnetic field can be formed by applying voltages VU, VV and VW to first to third coils 58, respectively, and rotor 52 can be rotated by attractive force and repulsion force between the plurality of magnetic elements 57 and the plurality of permanent magnets 53 in rotor 52. As rotor 52 rotates, impeller 10 rotates as a result of attractive force from the plurality of permanent magnets 51 in rotor 52 and the plurality of permanent magnets 50 in impeller 10.

Here, when impeller 10 is rotating at a rated rotation speed, attractive force between permanent magnets 15a, 15b and permanent magnets 16a, 16b and attractive force between the plurality of permanent magnets 50 and the plurality of permanent magnets 51 are set to be balanced with each other substantially around the center of the movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be lowered. In addition, a surface of impeller 10 and a surface of the inner wall of housing 2 are not damaged (no projections and recesses in the surfaces) during the relative slide, and moreover, impeller 10 is readily levitated from housing 2 without contacting even when hydrodynamic pressure is small during low-speed rotation.

In addition, as in the first embodiment, a plurality of grooves for hydrodynamic bearing 21 are formed in the surface of diaphragm 6 facing shroud 12 of impeller 10, and a plurality of grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

In addition, in this second embodiment, as shown in FIG. 13, attractive force F1 between permanent magnets 15a, 15b and permanent magnets 16a, 16b decreases as impeller 10 moves in the radial direction. Similarly, attractive force F2 between permanent magnets 50 and 51 decreases as impeller 10 moves in the radial direction.

During a desired pump operation, impeller 10 is eccentric in the radial direction. Therefore, when amount of change $\Delta F1$ in attractive force F1 with respect to an amount of eccentricity of impeller 10 is different from amount of change $\Delta F2$ in attractive force F2 with respect to the amount of eccentricity of impeller 10, a levitation position of impeller 10 at that eccentric position is displaced from the central position in blood chamber 7. Therefore, any one gap of the gap between impeller 10 and the inner wall of blood chamber 7 and the gap between impeller 10 and diaphragm 6 becomes narrow, and impeller 10 is brought into contact with the inner wall of blood chamber 7 or with diaphragm 6 even by action of small disturbance on impeller 10.

On the other hand, in a case where amount of change $\Delta F1$ in attractive force F1 is equal to amount of change $\Delta F2$ in attractive force F2, even though impeller 10 is eccentric in the radial direction, a levitation position of impeller 10 is maintained at the central position in blood chamber 7. Therefore, even when disturbance acts on impeller 10, it is less likely that impeller 10 comes in contact with the inner wall of blood chamber 7 or diaphragm 6. Then, in this second embodiment, by adjusting a diameter of permanent magnet 50, 51, relation of $\Delta F1 \approx \Delta F2$ is satisfied. Thus, even when impeller 10 is eccentric in the radial direction, a levitation position of impeller 10 in the axial direction is kept at the central position in blood chamber 7.

Figure 27:
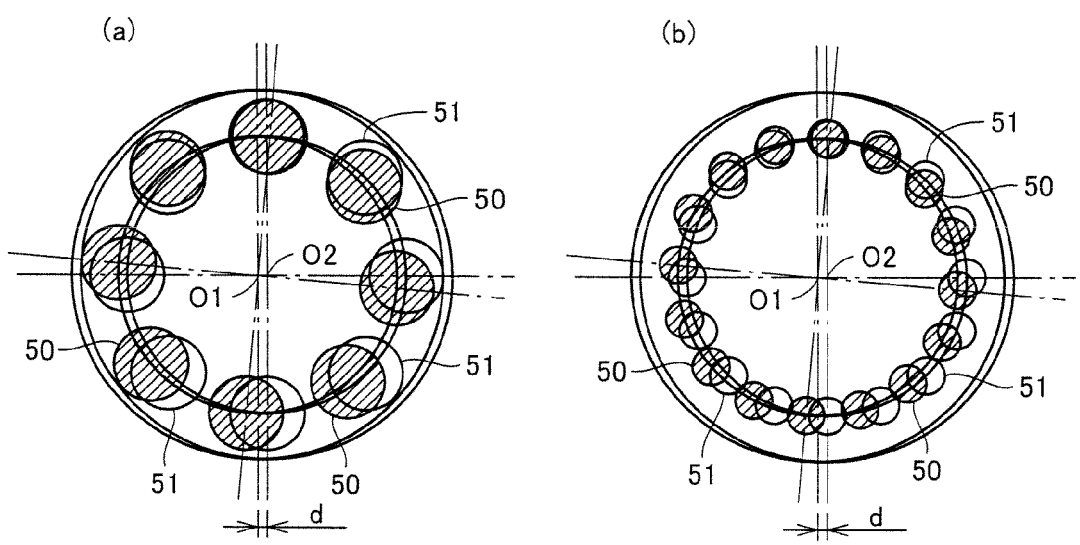
FIG. 27 is a diagram for illustrating relation between a diameter of a permanent magnet 50, 51 shown in FIG. 26 and eccentricity of the impeller.
Figure 28:
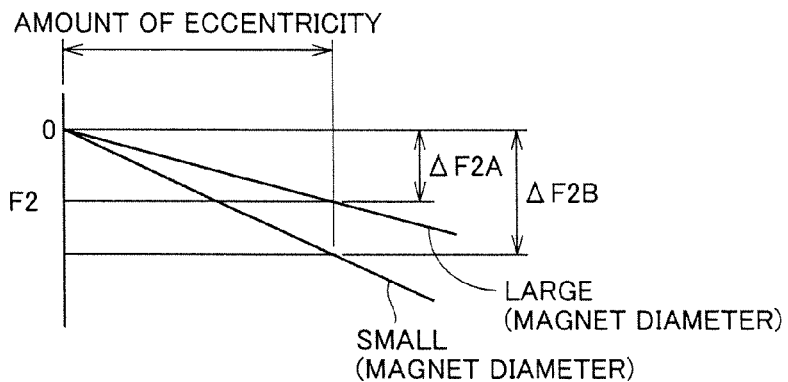
FIG. 28 is a diagram showing relation between attractive force F2 between permanent magnets 50 and 51 shown in FIG. 27 and an amount of eccentricity of the impeller.

FIGS. 27 (a) and (b) are diagrams showing a state of overlapping between permanent magnets 50 and 51 when impeller 10 is eccentric. FIG. 27 (a) shows a case where a diameter of permanent magnet 50, 51 is relatively large, and FIG. 27 (a) shows a case where a diameter of permanent magnet 50, 51 is relatively small. FIG. 28 is a diagram showing relation between an amount of eccentricity of impeller 10 and attractive force F2.

In FIGS. 27 (a) and (b), a center of rotation of the plurality of permanent magnets 50 is denoted as O1, while a center of rotation of the plurality of permanent magnets 51 is denoted as O2. When impeller 10 is not eccentric, centers of rotation O1 and O2 match with each other when viewed in a direction perpendicular to impeller 10. Here, it is assumed that centers of rotation O1 and O2 are displaced from each other by a certain distance d as a result of eccentricity of impeller 10.

In a case of the centrifugal blood pump shown in FIG. 26, as rotor 52 rotates, difference in angle is caused between permanent magnets 50 and 51, and hence rotational torque is generated in impeller 10. When impeller 10 is not eccentric, facing areas (overlapping areas) of a plurality of sets of permanent magnets 50 and 51 are equal thereamong. When impeller 10 is eccentric, as shown in FIGS. 27 (a) and (b), facing areas of permanent magnets 50, 51 increase or decrease from one set to another, however, the sum of facing areas of the plurality of sets of permanent magnets 50 and 51 decreases as compared with a case where impeller 10 is not eccentric. In a case where impeller 10 is eccentric, an amount of change in the sum of the facing areas of the plurality of sets of permanent magnets 50 and 51 is greater as the diameter of permanent magnet 50, 51 is smaller.

Attractive force F2 between the plurality of sets of permanent magnets 50 and 51 varies in accordance with the sum of the facing areas of the plurality of sets of permanent magnets 50 and 51. Therefore, as shown in FIG. 28, attractive force F2 decreases with displacement of impeller 10 in the radial direction. An amount of displacement $\Delta F2A$ in attractive force F2 in a case where a diameter of permanent magnet 50, 51 is relatively large is smaller than an amount of displacement $\Delta F2B$ in attractive force F2 in a case where a diameter of permanent magnet 50, 51 is relatively small. On the other hand, when a dimension of permanent magnets 15a, 15b and permanent magnets 16a, 16b is determined, amount of change $\Delta F1$ in attractive force F1 between permanent magnets 15a, 15b and permanent magnets 16a, 16b is constant. Therefore, by adjusting a diameter of permanent magnet 50, 51, amount of change $\Delta F1$ in attractive force F1 can substantially match with amount of change $\Delta F2$ in attractive force F2.

In addition, an amount of displacement between a central point of permanent magnet 50 and a central point of permanent magnet 51 is the sum of an amount of eccentricity of impeller 10 and an amount of displacement in angle in a circumferential direction generated by desired rotational torque, and an amount of displacement between center of rotation O1 of permanent magnet 50 and center of rotation O2 of permanent magnet 51 is equal to the amount of eccentricity of impeller 10. On the other hand, an amount of displacement between the center of rotation of permanent magnets 15a, 15b and the center of rotation of permanent magnets 16a, 16b is equal to the amount of eccentricity of impeller 10.

Therefore, in order to make amount of change ΔF1 in attractive force F1 equal to amount of change ΔF2 in attractive force F2, an absolute value K1 of a positive supporting rigidity value in the radial direction of the magnetic coupling portion constituted of permanent magnets 15a, 15b and permanent magnets 16a, 16b and an absolute value K2 of a positive supporting rigidity value in the radial direction of the magnetic coupling portion constituted of the plurality of sets of permanent magnets 50 and 51 desirably keep relation of K1−K2>0.

In this second embodiment, attractive force between permanent magnets 15a, 15b and permanent magnets 16a, 16b and attractive force between the plurality of permanent magnets 50 and the plurality of permanent magnets 51 are balanced with each other and grooves for hydrodynamic bearing 21, 22 are provided. Therefore, a levitation position of impeller 10 can always be maintained at the substantially central position in housing 2. In addition, since two pairs of permanent magnets 15a, 16a and permanent magnets 15b, 16b are provided in the radial direction of impeller 10, rigidity for supporting impeller 10 in the radial direction can be increased as compared with a case where only a pair of permanent magnets is provided in the radial direction of impeller 10. Further, since amount of change ΔF1 in attractive force F1 between permanent magnets 15a, 15b and permanent magnets 16a, 16b and amount of change ΔF2 in attractive force F2 between the plurality of sets of permanent magnets 50, 51 when impeller 10 is eccentric substantially match with each other, a levitation position of impeller 10 can always be maintained at the substantially central position in housing 2. Therefore, mechanical contact between impeller 10 and housing 2 can be lessened and hence occurrence of hemolysis or thrombus can be prevented.

In this second embodiment, relation of ΔF1≈ΔF2 is satisfied by adjusting a diameter of permanent magnet 50, 51 and by adjusting amount of change ΔF2 in attractive force F2. Relation of ΔF1≈ΔF2 may be satisfied, however, by adjusting a dimension of permanent magnets 15a, 15b and permanent magnets 16a, 16b (for example, a width, an interval in the radial direction) and by adjusting amount of change ΔF1 in attractive force F1.

Figure 29:
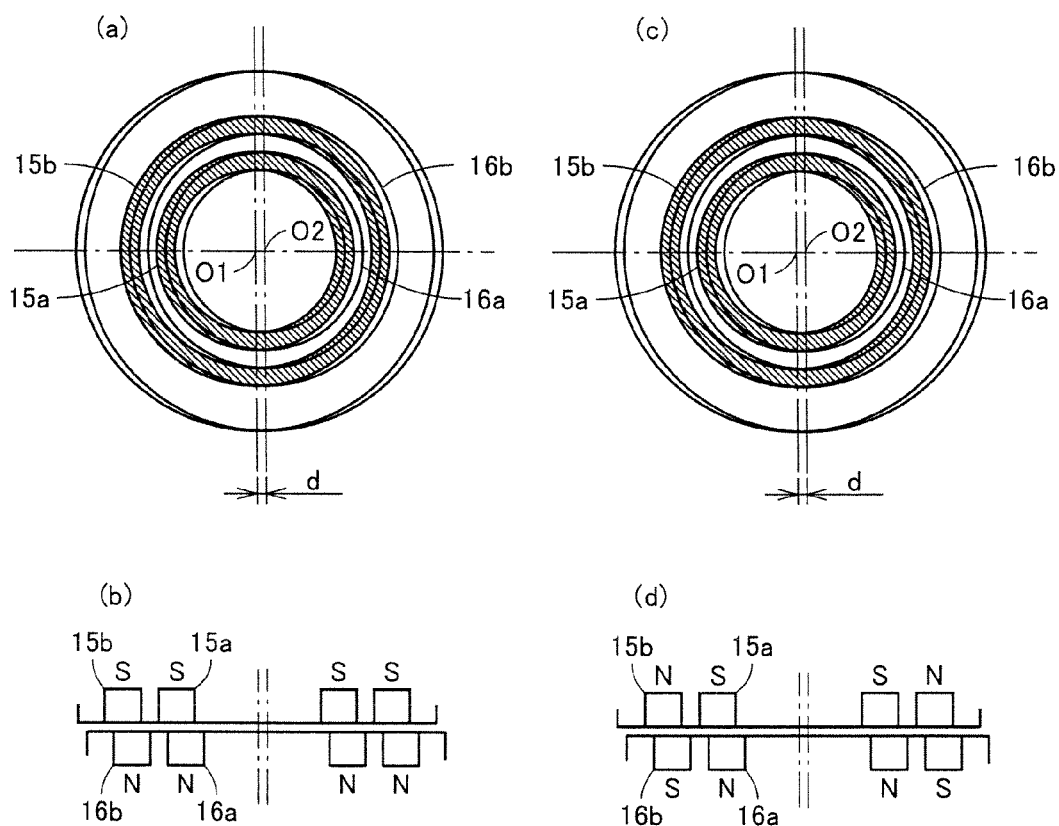
FIG. 29 is a diagram showing a modification of the second embodiment.

FIGS. 29 (a) and (b) are diagrams showing a modification of the second embodiment and showing a state of overlapping between permanent magnets 15a, 15b and permanent magnets 16a, 16b when impeller 10 is eccentric. FIG. 27 (a) shows a case where magnetic poles of permanent magnets 15a, 15b (permanent magnets 16a, 16b) are oriented in the same direction, while FIG. 27 (b) shows a case where magnetic poles of permanent magnets 15a, 15b (permanent magnets 16a, 16b) are oriented in directions opposite to each other. FIG. 28 is a diagram showing relation between an amount of eccentricity of impeller 10 and attractive force F1.

In FIGS. 29 (a) and (b), a center of rotation of permanent magnets 15a, 15b is denoted as O1, while a center of rotation of permanent magnets 16a, 16b is denoted as O2. When impeller 10 is not eccentric, centers of rotation O1 and O2 match with each other when viewed in a direction perpendicular to impeller 10. Here, it is assumed that centers of rotation O1 and O2 are displaced from each other by certain distance d as a result of eccentricity of impeller 10.

Figure 30:
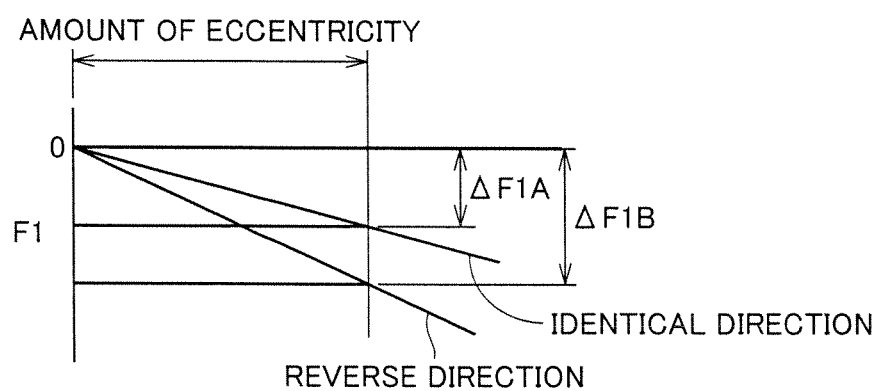
FIG. 30 is a diagram showing relation between attractive force F1 between permanent magnets 15a, 15b and permanent magnets 16a, 16h shown in FIG. 29 and an amount of eccentricity of the impeller.

When impeller 10 is eccentric, as shown in FIGS. 29 (a) to (d), a facing area of permanent magnets 15a, 16a and permanent magnets 15b, 16b decreases as compared with a case where impeller 10 is not eccentric. In addition, attractive force F1 between permanent magnets 15a, 15b and permanent magnets 16a, 16b varies in accordance with a facing area of permanent magnets 15a, 16a and permanent magnets 15b, 16b. Further, when impeller 10 is eccentric, in a case of FIGS. 29 (a) and (b), attractive force is generated between permanent magnets 15a and 16b and between 15b and 16a, whereas in a case of FIGS. 29 (c) and (d), repulsion force is generated between permanent magnets 15a and 16b and between 15b and 16a. Therefore, as shown in FIG. 30, attractive force F1 decreases as impeller 10 is displaced in the radial direction, and an amount of displacement ΔF1B in the case of FIGS. 29 (c) and (d) is greater than an amount of displacement ΔF1A in the case of FIGS. 29 (a) and (b).

In this modification, magnetic poles of permanent magnets 15a, 15b and permanent magnets 16a, 16b are arranged as shown in FIGS. 29 (a) and (b) or FIGS. 29 (c) and (d), so that amount of change ΔF1 in attractive force F1 is adjusted and then amount of change ΔF2 in attractive force F2 is adjusted with the method shown in the second embodiment. The effect the same as in the second embodiment is obtained also in this modification.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST 1 pump unit; 2 housing; 3 body portion; 4 blood inlet port; 5 blood outlet port; 6 diaphragm; 7 blood chamber; 8 motor chamber; 10 impeller; 10a through hole; 11, 12 shroud; 13 vane; 14 blood passage; 15a, 15b, 16a, 16b, 17, 41, 50, 51, 53 permanent magnet; 18, 35, 37 to 40, 57 magnetic element; 19, 31, 56 yoke; 20, 58 coil; 21, 22 groove for hydrodynamic bearing; 25 controller; 26 amplitude operation unit; 27 comparator; 28 storage unit; 29 motor control circuit; 30 power amplifier; 52 rotor; 54 bearing; 55 central axis; and SE magnetic sensor.

The invention claimed is:

1. A centrifugal pump apparatus including a housing having first and second chambers partitioned from each other by a diaphragm, an impeller rotatably provided in said first chamber along said diaphragm, for delivering liquid by centrifugal force during rotation, and a drive unit provided in said second chamber for driving said impeller to rotate, comprising:

a first magnetic element provided in one surface of said impeller;

a second magnetic element provided in an inner wall of said first chamber facing the one surface of said impeller, for attracting said first magnetic element; and a third magnetic element provided in the other surface of said impeller, during rotation of said impeller, a first attractive force between said first and second magnetic elements and a second attractive force between said third magnetic element and said drive unit being balanced with each other substantially in a center of a movable range of said impeller in said first chamber, and an amount of change in said first attractive force with respect to an amount of eccentricity in a radial direction of said impeller being substantially equal to an amount of change in said second attractive force with respect to the amount of eccentricity in the radial direction of said impeller by adjustment of the second attractive force by modulation of phase of voltages supplied to the drive unit, and a first groove for hydrodynamic bearing being formed in one surface of said impeller or in the inner wall of said first chamber facing the one surface and a second groove for hydrodynamic bearing being formed in the other surface of said impeller or in said diaphragm facing the other surface.

2. The centrifugal pump apparatus according to claim 1, wherein said drive unit includes a rotor rotatably provided along said diaphragm in said second chamber, a fourth magnetic element provided in said rotor, for attracting said third magnetic element, and a motor for rotating said rotor.

3. The centrifugal pump apparatus according to claim 2, wherein an absolute value of a positive supporting rigidity value in the radial direction of a magnetic coupling portion constituted of said first and second magnetic elements is greater than an absolute value of a positive supporting rigidity value in a radial direction of a magnetic coupling portion constituted of said third and fourth magnetic elements.

4. The centrifugal pump apparatus according to claim 1, wherein said third magnetic element includes a plurality of magnets arranged along a single, identical circle such that adjacent magnetic polarities are different from each other, and said drive unit includes a plurality of coils provided to face said plurality of magnets, for generating rotating magnetic field.

5. The centrifugal pump apparatus according to claim 4, wherein said second attractive force is adjusted by varying a phase of a current fed to said plurality of coils.

6. The centrifugal pump apparatus according to claim 5, further comprising a magnetic sensor provided in said second chamber to face said plurality of magnets, wherein a phase of a current fed to said plurality of coils is varied based on an output signal from said magnetic sensor.

7. The centrifugal pump apparatus according to claim 1, wherein said third magnetic element includes a plurality of magnets arranged along a single, identical circle such that adjacent magnetic polarities are different from each other, and said drive unit includes a plurality of fourth magnetic elements provided to face said plurality of magnets, and a plurality of coils provided in correspondence with said plurality of fourth magnetic elements respectively and each wound around the corresponding fourth magnetic element, for generating rotating magnetic field.

8. The centrifugal pump apparatus according to claim 7, wherein said second attractive force is adjusted by varying a phase of a current fed to said plurality of coils.

9. The centrifugal pump apparatus according to claim 8, further comprising a magnetic sensor provided in said second chamber to face said plurality of magnets, wherein a phase of a current fed to said plurality of coils is varied based on an output signal from said magnetic sensor.

10. The centrifugal pump apparatus according to claim 1, comprising:

a plurality of said first magnetic elements provided in one surface of said impeller and aligned in a radial direction of said impeller; and a plurality of said second magnetic elements provided in the inner wall of said first chamber facing the one surface of said impeller and attracting said plurality of first magnetic elements respectively, wherein during rotation of said impeller, first attractive force between said plurality of first magnetic elements and said plurality of second magnetic elements and second attractive force between said third magnetic element and said drive unit are balanced with each other substantially in the center of the movable range of said impeller in said first chamber.

11. The centrifugal pump apparatus according to claim 10, wherein at least one magnetic element of said plurality of first magnetic elements and said plurality of second magnetic elements is formed annularly around a rotation centerline of said impeller.

12. The centrifugal pump apparatus according to claim 10, wherein at least one magnetic element of said plurality of first magnetic elements and said plurality of second magnetic elements are formed as multiple pieces annularly around a rotation centerline of said impeller.

13. The centrifugal pump apparatus according to claim 10, wherein each of said plurality of first magnetic elements and said plurality of second magnetic elements is a permanent magnet, and N poles of two first magnetic elements adjacent in said radial direction of said impeller are oriented in an identical direction.

14. The centrifugal pump apparatus according to claim 10, wherein each of said plurality of first magnetic elements and said plurality of second magnetic elements is a permanent magnet, and N poles of two first magnetic elements adjacent in said radial direction of said impeller are oriented in directions different from each other.

15. The centrifugal pump apparatus according to claim 10, wherein an interval between two first magnetic elements adjacent in said radial direction of said impeller is greater than $\frac{1}{2}$ of a movable distance of said impeller in the radial direction in said first chamber.

16. The centrifugal pump apparatus according to claim 10, wherein a plurality of said third magnetic elements are provided, said plurality of third magnetic elements are arranged along a single, identical circle such that adjacent magnetic polarities are different from each other, and said drive unit includes a plurality of coils provided to face said plurality of third magnetic elements, for generating rotating magnetic field.

17. The centrifugal pump apparatus according to claim 10, wherein a plurality of said third magnetic elements are provided, said plurality of third magnetic elements are arranged along a single, identical circle such that adjacent magnetic polarities are different from each other, and said drive unit includes a plurality of fourth magnetic elements arranged to face said plurality of third magnetic elements, and a plurality of coils provided in correspondence with said plurality of fourth magnetic elements respectively and each wound around the corresponding fourth magnetic element, for generating rotating magnetic field.

18. The centrifugal pump apparatus according to claim 10, wherein said drive unit includes a rotor rotatably provided along said diaphragm in said second chamber, a fourth magnetic element provided in said rotor to face said third magnetic element, for attracting said third magnetic element, and a motor for rotating said rotor.

19. The centrifugal pump apparatus according to claim 1, wherein said liquid is blood, and said centrifugal pump apparatus is used for circulating said blood.

20. A centrifugal pump apparatus including a housing having first and second chambers partitioned from each other by a diaphragm, an impeller rotatably provided in said first chamber along said diaphragm, for delivering liquid by centrifugal force during rotation, and a control unit for supplying multi-phase drive voltages to coils of a drive unit of the apparatus for driving said impeller to rotate, comprising:

a first magnetic element provided in one surface of said impeller;

a second magnetic element provided in an inner wall of said first chamber facing the one surface of said impeller, for attracting said first magnetic element; and a third magnetic element provided in the other surface of said impeller, during rotation of said impeller, a first attractive force between said first and second magnetic elements and a second attractive force between said third magnetic element and said drive unit being balanced with each other substantially in a center of a movable range of said impeller in said first chamber, and an amount of change in said first attractive force with respect to an amount of eccentricity in a radial direction of said impeller being substantially equal to an amount of change in said second attractive force with respect to the amount of eccentricity in the radial direction of said impeller by adjustment of the second attractive force by modulation of phase of drive voltages supplied to the coils of the drive unit.

21. The centrifugal pump apparatus according to claim 20, wherein the control unit comprises a motor control circuit and a power amplifier, and wherein the motor control circuit outputs three-phase control signals to the power amplifier and the power amplifier amplifies the three-phase control signals and generates three-phase drive voltages that are supplied to first, second, and third coils of the drive unit for adjustment of the second attractive force during rotation of said impeller.

* * * * *